United States Patent [19]

Bushell et al.

[11] Patent Number: 5,196,610

[45] Date of Patent: Mar. 23, 1993

[54] INSECTICIDAL ETHERS

[75] Inventors: Michael J. Bushell, Wokingham; Alan J. Whittle, Aldershot; Robin A. E. Carr, Camberley, all of England

[73] Assignee: Imperial Chemical Industries PLC, London, England

[21] Appl. No.: 891,350

[22] Filed: Jul. 31, 1986

[30] Foreign Application Priority Data

Aug. 9, 1985 [GB] United Kingdom ................ 8520027

[51] Int. Cl.$^5$ ............................................. C07C 41/00
[52] U.S. Cl. ..................................... 568/661; 568/633; 568/634; 568/649; 564/305; 564/346; 546/339; 549/362; 549/505
[58] Field of Search ............... 568/661, 633, 634, 649; 564/305, 346; 549/362, 508

[56] References Cited

U.S. PATENT DOCUMENTS

| 4,542,243 | 9/1985 | Umemoto | 562/661 |
| 4,552,894 | 11/1985 | Inoue | 562/661 |
| 4,678,811 | 7/1987 | Franke et al. | 514/721 |

FOREIGN PATENT DOCUMENTS

| 2418571 | 11/1974 | Fed. Rep. of Germany | 568/661 |
| 2418572 | 11/1974 | Fed. Rep. of Germany | 568/661 |
| 2518019 | 11/1975 | Fed. Rep. of Germany | 568/661 |
| 3438483 | 4/1986 | Fed. Rep. of Germany | 568/661 |

Primary Examiner—Paul J. Killos
Attorney, Agent, or Firm—Cushman, Darby & Cushman

[57] ABSTRACT

A compound of formula:

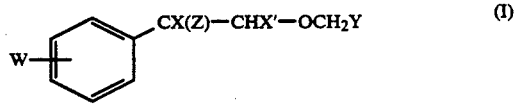

(I)

wherein W represents one or two substituents selected from halo, alkyl, alkoxy, alkoxyalkyl, haloalkyl and haloalkoxy, or W represents a bidentate group linking adjacent carbon atoms selected from alkylene and alkylenedioxy; Z represents a fluoroalkyl group of up to two carbon atoms; Y represents a substituted aryl group where such substituent is selected from halo, alkyl, aryl, aralkyl, aryloxy and arylamino; and either X' is hydrogen and X is selected from hydrogen, halo, hydroxy, alkoxy and aryloxy, or X and X' together represent a second bond between the adjacent carbon atoms. The compounds have useful insecticidal properties.

19 Claims, No Drawings

INSECTICIDAL ETHERS

This invention relates to novel fluorinated ethers useful as insecticides and their preparation, to insecticidal compositions thereof and to methods of combating and controlling insect pests therewith.

In a first aspect the invention provides compounds of formula:

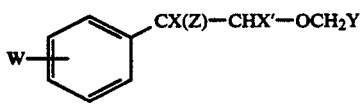

where W represents one or two substituents selected from halo, alkyl, alkoxy, alkoxyalkyl, haloalkyl and haloalkoxy, or W represents a bidentate group linking adjacent carbon atoms selected from alkylene and alkylenedioxy; Z represents a fluoroalkyl group of up to two carbon atoms; Y represents a substituted aryl group where each substituent is selected from halo, alkyl, aryl, aralkyl, aryloxy and arylamino; and either X' is hydrogen and X is selected from hydrogen, halo, hydroxy, alkoxy and acyloxy, or X and X' together represent a second bond between the adjacent carbon atoms.

Preferred compounds are those wherein Z represents the trifluoromethyl group, W represents fluoro, chloro, bromo, alkyl of up to four carbon atoms, alkoxy of up to four carbon atoms, alkoxyalkyl of up to a total of four carbon atoms, fluoroalkyl of up to two carbon atoms, fluoroalkoxy of up to two carbon atoms, alkylene of three or four carbon atoms, or alkylenedioxy of up to two carbon atoms, and Y represents an aryl group selected from phenyl, pyridyl and furyl substituted with fluoro, methyl, phenyl, benzyl, phenoxy, chlorophenoxy, fluorophenoxy, bromophenoxy or fluoroanilino.

Particularly preferred compounds are those wherein Z represents trifluoromethyl, W represents a substituent in the 4-position selected from chloro, methoxy, ethoxy, trifluoromethyl, trifluoromethoxy, and difluoromethoxy, Y represents a -phenoxyphenyl group in which each phenyl group may be unsubstituted or substituted with halogen, X' is hydrogen and X is selected from hydrogen, fluoro or chloro.

Particular examples of compounds according to the invention include those set out in Tables I and II below. In Table I the compounds conform to the formula:

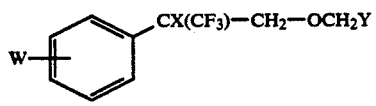

and in Table II to the formula:

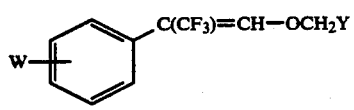

In these Tables Y is defined as $R^1$ to $R^{14}$ wherein $R^1$ to $R^{14}$ represent the following groups:
$R^1$: 3-phenoxyphenyl
$R^2$: 3-(4-chlorophenoxy)phenyl
$R^3$: 4-fluoro-3-phenoxyphenyl
$R^4$: 3-(4-bromophenoxy)phenyl
$R^5$: 4-fluoro-3-(4-bromophenoxy)phenyl
$R^6$: 4-fluoro-3-(4-chlorophenoxy)phenyl
$R^7$: 3-(2,4-difluorophenoxy)phenyl
$R^8$: 3-benzylphenyl
$R^9$: 3-benzyl-4-fluorophenyl
$R^{10}$: 3-(4-fluorophenylamino)phenyl
$R^{11}$: 6-phenoxypyrid-2-yl
$R^{12}$: 2-methyl-3-phenylphenyl
$R^{13}$: 4-methyl-2,3,5,6-tetrafluorophenyl
$R^{14}$: 5-benzylfuran-3-yl All of the compounds listed in Table 1 are of racemic mixtures Of the two optically active isomers (the R- and S-isomers), and all of the compounds in Table II can exist as E- and Z-isomers (or mixtures thereof). It is to be understood that the invention includes within its scope not only the above isomer mixtures but also any single isomer of an invention compound.

TABLE I

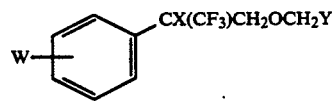

| Compound No. | W | X | Y |
|---|---|---|---|
| 1 | 4-OC$_2$H$_5$ | H | $R^1$ |
| 2 | 4-OC$_2$H$_5$ | H | $R^{13}$ |
| 3 | 4-OC$_2$H$_5$ | H | $R^2$ |
| 4 | 4-OC$_2$H$_5$ | H | $R^{11}$ |
| 5 | 4-OC$_2$H$_5$ | H | $R^6$ |
| 6 | 4-OC$_2$H$_5$ | H | $R^5$ |
| 7 | 4-OC$_2$H$_5$ | H | $R^{12}$ |
| 8 | 4-OC$_2$H$_5$ | H | $R^9$ |
| 9 | 4-OC$_2$H$_5$ | H | $R^4$ |
| 10 | 4-OC$_2$H$_5$ | H | $R^7$ |
| 11 | 4-OC$_2$H$_5$ | H | $R^{10}$ |
| 12 | 4-OC$_2$H$_5$ | H | $R^8$ |
| 13 | 3-F,4-OC$_2$H$_5$ | H | $R^2$ |
| 14 | 3-F,4-OC$_2$H$_5$ | H | $R^1$ |
| 15 | 4-Cl | H | $R^3$ |
| 16 | 4-Cl | H | $R^1$ |
| 17 | 2,4-Cl$_2$ | H | $R^1$ |
| 18 | 4-F | H | $R^3$ |
| 19 | 3,4-(CH$_2$)$_3$ | H | $R^3$ |
| 20 | 4-(CH$_2$)$_2$CH$_3$ | H | $R^3$ |
| 21 | 4-C(CH$_3$)$_3$ | H | $R^3$ |
| 22 | 4-CH$_3$ | H | $R^1$ |
| 23 | 4-CH$_2$OCH$_3$ | H | $R^2$ |
| 24 | 4-CH$_2$OCH$_3$ | H | $R^1$ |
| 25 | 4-OCF$_3$ | H | $R^3$ |
| 26 | 4-OCF$_3$ | H | $R^2$ |
| 27 | 4-OCF$_3$ | H | $R^1$ |
| 28 | 4-OCF$_3$ | H | $R^{11}$ |
| 29 | 4-OCH$_3$ | H | $R^3$ |
| 30 | 4-OCH$_3$ | H | $R^1$ |
| 31 | 3,4-(OCH$_2$O) | H | $R^1$ |
| 32 | 3,4-(OCH$_2$O) | H | $R^2$ |
| 33 | 4-OC$_2$H$_5$ | H | $R^3$ |
| 34 | 4-CF$_3$ | H | $R^1$ |
| 35 | 4-Br | H | $R^3$ |
| 36 | 4-CF$_3$ | H | $R^3$ |
| 37 | 4-OC$_2$H$_5$ | H | $R^{14}$ |
| 38 | 4-OC$_2$H$_5$ | Cl | $R^1$ |
| 39 | 4-OC$_2$H$_5$ | Cl | $R^{13}$ |
| 40 | 4-OC$_2$H$_5$ | Cl | $R^3$ |
| 41 | 4-OC$_2$H$_5$ | Cl | $R^{11}$ |
| 42 | 4-OC$_2$H$_5$ | Cl | $R^2$ |
| 43 | 4-OC$_2$H$_5$ | Cl | $R^5$ |
| 44 | 4-OC$_2$H$_5$ | Cl | $R^6$ |
| 45 | 4-OC$_2$H$_5$ | Cl | $R^{14}$ |
| 46 | 4-OC$_2$H$_5$ | Cl | $R^{12}$ |
| 47 | 4-OC$_2$H$_5$ | Cl | $R^9$ |
| 48 | 3-F,4-OC$_2$H$_5$ | Cl | $R^2$ |
| 49 | 3-F,4-OC$_2$H$_5$ | Cl | $R^1$ |
| 50 | 4-Cl | Cl | $R^3$ |

TABLE I-continued

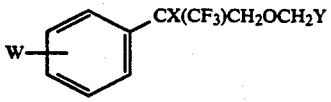

| Compound No. | W | X | Y |
|---|---|---|---|
| 51 | 4-F | Cl | $R^3$ |
| 52 | 3,4-(CH₂)₃ | Cl | $R^3$ |
| 53 | 4-(CH₂)₂CH₃ | Cl | $R^3$ |
| 54 | 4-C(CH₃)₃ | Cl | $R^3$ |
| 55 | 4-CH₃ | Cl | $R^1$ |
| 56 | 4-CH₂OCH₃ | Cl | $R^2$ |
| 57 | 4-CH₂OCH₃ | Cl | $R^1$ |
| 58 | 4-OCF₃ | Cl | $R^3$ |
| 59 | 4-OCF₃ | Cl | $R^1$ |
| 60 | 4-OCF₃ | Cl | $R^2$ |
| 61 | 4-OCF₃ | Cl | $R^{11}$ |
| 62 | 4-OCH₃ | Cl | $R^3$ |
| 63 | 4-OCH₃ | Cl | $R^1$ |
| 64 | 3,4-(OCH₂O) | Cl | $R^1$ |
| 65 | 3,4-(OCH₂O) | Cl | $R^2$ |
| 66 | 4-Cl | Cl | $R^1$ |
| 67 | 2,4-Cl₂ | Cl | $R^1$ |
| 68 | 4-CF₃ | Cl | $R^1$ |
| 69 | 4-Br | Cl | $R^3$ |
| 70 | 4-CF₃ | Cl | $R^3$ |
| 71 | 4-OC₂H₅ | Cl | $R^4$ |
| 72 | 4-OC₂H₅ | Cl | $R^7$ |
| 73 | 4-OC₂H₅ | Cl | $R^8$ |
| 74 | 4-OC₂H₅ | Cl | $R^{10}$ |
| 75 | 4-OC₂H₅ | F | $R^1$ |
| 76 | 4-OC₂H₅ | F | $R^{11}$ |
| 77 | 4-OC₂H₅ | F | $R^3$ |
| 78 | 4-OC₂H₅ | F | $R^{13}$ |
| 79 | 4-OC₂H₅ | F | $R^2$ |
| 80 | 4-OC₂H₅ | F | $R^{12}$ |
| 81 | 4-Cl | F | $R^3$ |
| 82 | 4-OCF₃ | F | $R^1$ |
| 83 | 4-Br | F | $R^3$ |
| 84 | 4-CF₃ | F | $R^1$ |
| 85 | 4-Cl | F | $R^1$ |
| 86 | 2,4-Cl₂ | F | $R^1$ |
| 87 | 4-CH₃ | F | $R^1$ |
| 88 | 4-OCH₃ | F | $R^1$ |
| 89 | 3-F,4-OC₂H₅ | F | $R^1$ |
| 90 | 3,4-(OCH₂O) | F | $R^1$ |
| 91 | 4-CH₂OCH₃ | F | $R^1$ |
| 92 | 3-F,4-OC₂H₅ | F | $R^2$ |
| 93 | 3,4-(OCH₂O) | F | $R^2$ |
| 94 | 4-OCF₃ | F | $R^2$ |
| 95 | 4-CH₂OCH₃ | F | $R^2$ |
| 96 | 4-F | F | $R^3$ |
| 97 | 4-C(CH₃)₃ | F | $R^3$ |
| 98 | 4-OCH₃ | F | $R^3$ |
| 99 | 4-(CH₂)₂CH₃ | F | $R^3$ |
| 100 | 3,4-(CH₂)₃ | F | $R^3$ |
| 101 | 4-OCF₃ | F | $R^3$ |
| 102 | 4-CF₃ | F | $R^3$ |
| 103 | 4-OC₂H₅ | F | $R^4$ |
| 104 | 4-OC₂H₅ | F | $R^5$ |
| 105 | 4-OC₂H₅ | F | $R^6$ |
| 106 | 4-OC₂H₅ | F | $R^7$ |
| 107 | 4-OC₂H₅ | F | $R^8$ |
| 108 | 4-OC₂H₅ | F | $R^9$ |
| 109 | 4-OC₂H₅ | F | $R^{10}$ |
| 110 | 4-OCF₃ | F | $R^{11}$ |
| 111 | 4-OC₂H₅ | F | $R^{14}$ |
| 112 | 4-OC₂H₅ | OH | $R^1$ |
| 113 | 4-OC₂H₅ | OH | $R^3$ |
| 114 | 4-OC₂H₅ | OH | $R^{13}$ |
| 115 | 4-OC₂H₅ | OH | $R^2$ |
| 116 | 4-OC₂H₅ | OH | $R^5$ |
| 117 | 4-OC₂H₅ | OH | $R^6$ |
| 118 | 4-OC₂H₅ | OH | $R^{14}$ |
| 119 | 4-OC₂H₅ | OH | $R^9$ |
| 120 | 4-CH₃ | OH | $R^1$ |
| 121 | 3-F,4-OC₂H₅ | OH | $R^2$ |
| 122 | 4-C(CH₃)₃ | OH | $R^3$ |
| 123 | 4-(CH₂)₂CH₃ | OH | $R^3$ |
| 124 | 3,4-(CH₂)₃ | OH | $R^3$ |

TABLE I-continued

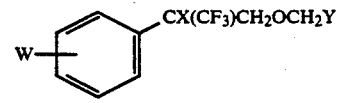

| Compound No. | W | X | Y |
|---|---|---|---|
| 125 | 4-F | OH | $R^3$ |
| 126 | 4-Cl | OH | $R^3$ |
| 127 | 4-Br | OH | $R^3$ |
| 128 | 3,4-(OCH₂O) | OH | $R^1$ |
| 129 | 3,4-(OCH₂O) | OH | $R^2$ |
| 130 | 4-OCH₃ | OH | $R^1$ |
| 131 | 4-OCH₃ | OH | $R^3$ |
| 132 | 4-CH₂OCH₃ | OH | $R^2$ |
| 133 | 4-CH₂OCH₃ | OH | $R^1$ |
| 134 | 4-OCF₃ | OH | $R^3$ |
| 135 | 4-OCF₃ | OH | $R^2$ |
| 136 | 4-OCF₃ | OH | $R^{11}$ |
| 137 | 4-CF₃ | OH | $R^1$ |
| 138 | 4-CF₃ | OH | $R^3$ |
| 139 | 4-OCF₃ | OH | $R^1$ |
| 140 | 3-F,4-OC₂H₅ | OH | $R^1$ |
| 141 | 4-OC₂H₅ | OH | $R^{11}$ |
| 142 | 4-OC₂H₅ | OH | $R^{12}$ |
| 143 | 4-Cl | OH | $R^1$ |
| 144 | 2,4-Cl₂ | OH | $R^2$ |
| 145 | 4-OC₂H₅ | OH | $R^4$ |
| 146 | 4-OC₂H₅ | OH | $R^7$ |
| 147 | 4-OC₂H₅ | OH | $R^8$ |
| 148 | 4-OC₂H₅ | OH | $R^{10}$ |
| 149 | 4-OC₂H₅ | OCOCH₃ | $R^3$ |
| 150 | 4-OC₂H₅ | OCH₃ | $R^3$ |
| 151 | 4-OCHF₂ | H | $R^1$ |
| 152 | 4-OCHF₂ | H | $R^2$ |
| 153 | 4-OCHF₂ | H | $R^3$ |
| 154 | 4-OCHF₂ | Cl | $R^1$ |
| 155 | 4-OCHF₂ | Cl | $R^2$ |
| 156 | 4-OCHF₂ | Cl | $R^3$ |
| 157 | 4-OCHF₂ | F | $R^1$ |
| 158 | 4-OCHF₂ | F | $R^2$ |
| 159 | 4-OCHF₂ | F | $R^3$ |
| 160 | 4-OCHF₂ | OH | $R^1$ |
| 161 | 4-OCHF₂ | OH | $R^2$ |
| 162 | 4-OCHF₂ | OH | $R^3$ |

TABLE II

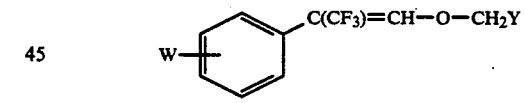

| Compound No. | W | Y |
|---|---|---|
| 163 | 4-Cl | $R^3$ |
| 164 | 3,4-(CH₂)₃ | $R^3$ |
| 165 | 4-(CH₂)₂CH₃ | $R^3$ |
| 166 | 4-C(CH₃)₃ | $R^3$ |
| 167 | 4-OCF₃ | $R^3$ |
| 168 | 4-OCF₃ | $R^1$ |
| 169 | 4-OCF₃ | $R^2$ |
| 170 | 4-OCHF₂ | $R^1$ |
| 171 | 4-OCHF₂ | $R^2$ |
| 172 | 4-OCHF₂ | $R^3$ |

It will be noted that the compounds of formula I fall into several types according to the nature of X and X'. These may be represented for the compounds of formula I wherein Z is trifluoromethyl as follows:

$$Ar—CH(CF_3)—CH_2—OCH_2Y \qquad (IA)$$

$$Ar—CF(CF_3)—CH_2—OCH_2Y \qquad (IB)$$

$$Ar—CCl(CF_3)—CH_2—OCH_2Y \qquad (IC)$$

 (ID)

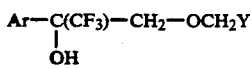 (IE)

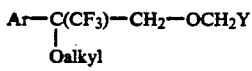 (IF)

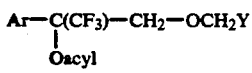 (IG)

wherein Ar represents the group of formula

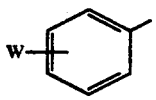

in formula I.

Compounds of formula (IE) may be converted to the corresponding compounds of formula IB, IC, ID, IF and IG by reaction with an appropriate reagent, and the compounds of formula IC and ID may be converted to the compounds of formula IA. Thus a compound of formula IB can be obtained by treating a compound of formula IE with a fluorinating agent such as diethylaminosulphur trifluoride (DAST), as follows:

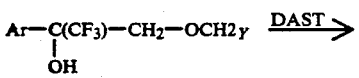

Ar—CF(CF$_3$)—CH$_2$—OCH$_2$Y

Similarly a compound of formula IC can be obtained by treating the corresponding compound of formula IE with a chlorinating agent such as thionyl chloride. Some compound of formula ID is also obtained in this process, presumably by dehydration of the hydroxy compound, and the two products can be separated by chromatographic means if desired.

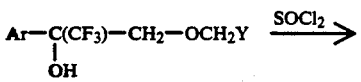

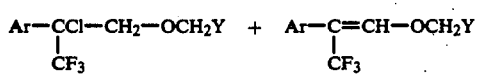

The compounds of formula IF and IG can be obtained by conventional O-alkylation and O-acylation techniques from the corresponding compounds of formula IE. Thus reaction with a base such as sodium hydride in an aprotic solvent and an alkyl halide gives the compound of formula IF, for example:

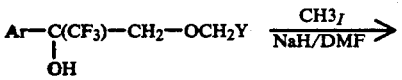

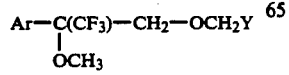

Similarly the compound of formula IG can be obtained by treating the corresponding compound of formula IE with an acyl halide or acyl anhydride in the presence of a base and a solvent, such as pyridine containing a catalytic amount of 4-dimethylaminopyridine (DMAP), for example:

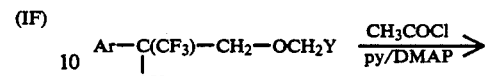

The preparation of the compounds of formula IE can be effected by a process in which either
(i) a compound of formula:

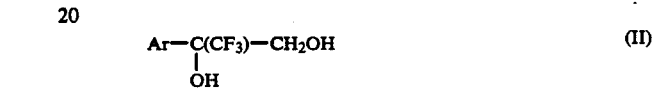 (II)

is reacted with a compound of formula YCH$_2$-Hal, where Hal represents a halogen atom such as chlorine or bromine, in the presence of phase transfer catalyst, or
(ii) a compound of formula:

 (III)

is reacted with a compound of formula YCH$_2$OH, where Hal represents a halogen atom such as chlorine or bromine, in the presence of a phase transfer catalyst, or
(iii) a compound of formula:

 (IV)

is reacted with a compound of formula YCH$_2$OH, in the presence of a base, such as sodium hydride and an aprotic solvent such as dimethylformamide.

The preparation of the compounds II, III and IV is outlined in the following scheme:

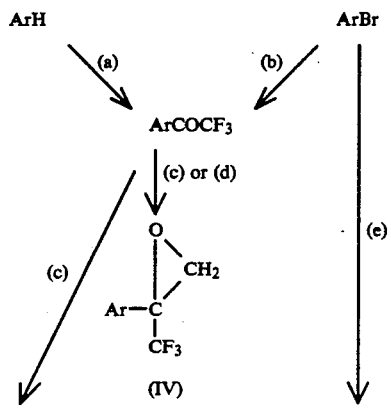

-continued

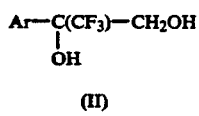
(II)

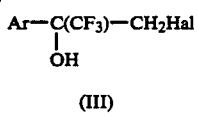
(III)

(a) CF₃COCl/AlCl₃
(b) Grignard reaction using CF₃CO₂H or (CF₃CO)₂O
(c) [(CH₃)₃SO]⁺.I⁻/KOH/t—BuOH
(d) [(CH₃)₃SO]⁺.I⁻/NaH/DMF
(e) Grignard reaction using CF₃-COCH₂Hal Further details of these processes, and variations thereof, are set forth in the Examples hereinafter.

The compounds of formula IA may also be prepared by reacting an alcohol of Formula:

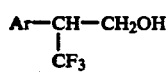   (V)

(- CF3
with a benzyl halide of formula YCH₂Hal where Hal represents chloro or bromo. The reaction preferably takes place in the presence of a base such as, for example, aqueous sodium hydroxide solution, and optionally in the presence of a quaternary ammonium salt which functions as a phase transfer catalyst.

The alcohols of formula V may be prepared by reduction of the acids of Formula:

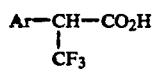   (VI)

in the form of an ester thereof, e.g. the lower alkyl ester such as the ethyl ester. Suitable reducing agents for the esters include aluminium hydrides such as lithium aluminium hydride or diisobutylaluminium hydride (DIBAL), but the actual choice is dependent upon the robustness of the substituents in the group Ar in the presence of the particular agent used.

The acids of formula VI may be prepared by various procedures. One process (which may be generally applicable with appropriate variation), which is illustrated in detail in the Examples hereinafter, is set out in outline in the following Scheme:

The compound of Formula (VII) may also be obtained by reacting a ketone of Formula:

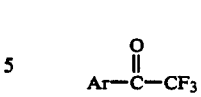

with chlorodifluoroacetic acid (in the form of a salt, e.g. the sodium salt) and triphenylphosphine, by a procedure similar to that shown in J. Org. Chem. (1967), vol. 32, page 1311. The esters of Formula VIII may also be prepared by reacting an aryl substituted malonate with a bromofluoromethane by the process similar to that shown in Tetrahedron Letters (1984), vol.25, page 1329, thus

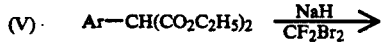

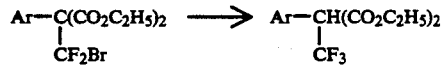

followed by partial saponification and decarboxylation. Alternatively the alcohols of formula V may be prepared by direct reduction of the epoxide of formula IV using, for example, borane-dimethylsulphide/boron trifluoride-diethyl ether complex, thus:

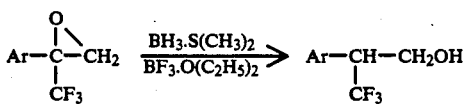

Many of the compounds of formulae II, III and IV are believed not to have been described before. In a further aspect therefore the invention provides each of the compounds of formulae:

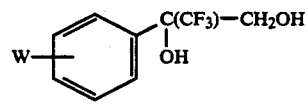

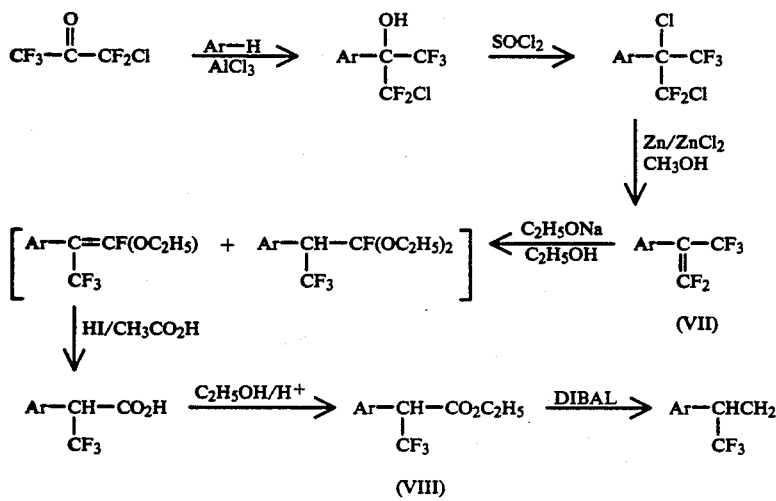

(VIII)

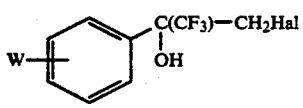

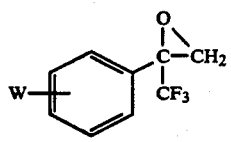

wherein W has any of the meanings given hereinbefore for the compounds of formula I.

Additionally the compounds of formulae V and VI have not been previously described. In a yet further aspect therefore the invention provides compounds of formulae:

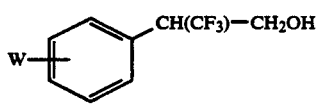

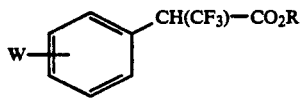

where W has any of the meanings given hereinbefore and R represents hydrogen or alkyl of up to four carbon atoms, such as methyl or ethyl.

The compounds of formula I may be used to combat and control infestations of insect pests and also other invertebrate pests, for example, acarine pests. The insect and acarine pets which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or Plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-biollethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion o diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemyins, for example such as abamectin, avermectin, and milbemycin;

(g) Hormones such as juvenile hormone, juvabione, or ecdysones.

(h) pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation Products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10-85% by weight of the ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
Myzus persicae (aphids)
Aphis fabae (aphids)
Megoura viceae (aphids)
Aedes aegypti (mosquitoes)
Dysdercus fasciatus (capsids)
Musca domestica (houseflies)
Pieris brassicae (white butterfly, larvae)
Plutella maculipennis (diamond back moth, larvae)
Phaedon cochleariae (mustard beetle)
Tetranychus cinnabarinus (carmine spider mite)
Tetranychus urticae (red spider mites)
Aonidiella spp. (scale insects)
Trialeuroides spp. (white flies)
Blattella germanica (cockroaches)
Spodoptera littoralis (cotton leaf worm)
Heliothis virescens (tobacco budworms)
Chortiocetes terminifera (locusts)
Diabrotica spp. (rootworms)
Agrotis spp. (cutworms)
Chilo partellus (maize stem borers)
Nilaparvata lugens (plant hoppers)

The compounds of formula I and compositions comprising them have shown themselves to be particularly useful in controlling pests of maize and rice such as Chilo (stem borers) as well as lepidopteran pests of cotton, for example Spodoptera spp. and Heliothis spp.

Although all of the invention compounds of formula I show insecticidal properties in the tests described hereinafter in the Examples they are not all equally effective at the particular rates tested to all of the test species. Thus it can be seen that the compounds of formula I wherein X is hydrogen, chloro or fluoro are usually more effective than those where X is hydroxy.

Some of the compounds are particularly useful for the control of insect pests of rice because they show high levels of activity against rice pests such as Chilo sp. and Nilaparvata sp. at rates which are not toxic to fish, thus enabling their use in paddy rice where fish are cultivated in the paddy.

In the following Examples, Gas Liquid Chromatography (GLC) retention times were determined on a Hewlett Packard 5890 Gas Chromatograph, using a Chromopak C.P. Sil 5 C.B. column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectrometry was performed at a frequency of 270 MHz on a Jeol FX 270 NMR spectrometer, unless otherwise stated. $^{19}$F NMR spectrometry was performed on a Jeol FX90Q spectrometer at a frequency of 84.26 MHz.

EXAMPLE 1

This Example illustrates the preparation of 4-bromo-α,α,α,-trifluoroacetophenone.

Literature reference: Journal of Organometallic Chemistry, 251, 139-148, (1983).

A mixture of 1,4-dibromobenzene (64 g), dry tetrahydrofuran (600 cm³) and dry diethyl ether (600 cm³) was cooled to −78° C. under an atmosphere of nitrogen. n-Butyllithium (108.4 cm³ of a 2.5 molar solution in hexane) was added to the stirred mixture over 40 minutes, the temperature of the reaction mixture being maintained below −72° C. by external cooling; the mixture was then stirred for a further 40 minutes. Methyl trifluoroacetate (35.4 g) was then added over 40 minutes, and stirring continued for a further 30 minutes, the temperature being maintained below −68° C. throughout. The reaction mixture was then carefully quenched by adding a mixture of concentrated hydrochloric acid (60 cm³) and ethanol (40 cm³), precooled to −78° C., over a period of 10 minutes. After stirring for a further 20 minutes, the reaction mixture was allowed to warm to the ambient temperature (ca. 22° C.). The organic layer was separated and concentrated by evaporation under reduced pressure to leave a water-contaminated oil (70 g). The oil was dissolved in diethyl ether, and the solution dried over anhydrous magnesium sulphate. Evaporation of the solvent under reduced pressure gave an orange oil, which was purified by distillation under reduced pressure (ca. 15 mm Hg). Two fractions containing essentially the same material, 4-bromo-α,α,α-trifluoroacetophenone, were obtained. The first fraction (17.19 g), boiling within a range of 78°–83° C., was shown to be 85% pure by gas liquid chromatography; the second fraction (41.13 g), boiling range 83°–84° C., was shown to be 99% pure by gas liquid chromatography. The second fraction crystallised on standing.

$^1$H NMR (CDCl$_3$)δ (ppm):7.7 (2H,m); 7.95 (2H,m)

$^{19}$F NMR (CDCl$_3$)δ (ppm—relative to CFCl$_3$):−72.1

EXAMPLE 2

By the use of a procedure similar to that illustrated in Example 1 above, the following compounds were prepared from the appropriate starting materials.

(i) 3-Fluoro-4-ethoxy-α,α,α-trifluoroacetophenone, from 4-bromo-2-fluorophenetole.

The preparation of 4-bromo-2-fluorophenetole is described in Example 42.

In this case, the product was purified by column chromatography on a silica gel support, eluting with n-hexane containing 5% by volume ethyl acetate.

$^1$H NMR (CDCl$_3$)δ (ppm):1.54 (3H,t); 4.2 (2H,q); 7.0 (1H,t); 7.7–7.95 (2H,m).

(ii) 4-Methoxymethyl-α,α,α-trifluoroacetophenone, from 4-bromobenzyl methyl ether.

The preparation of 4-bromobenzylmethyl ether is described in Example 41.

$^1$H NMR (CDCl$_3$)δ (ppm):3.45 (3H,s); 4.57 (2H,s); 7.5, 8.05 (4H,ABq)

IR (liquid film):1722 cm$^{-1}$ (C=O)

GLC retention time:1.67 minutes (iii) 3,4-(Methylenedioxy)-α,α,α-trifluoroacetophenone, from 4-bromo-1,2-(methylenedioxy)benzene.

$^1$H NMR (CDCl$_3$)δ (ppm): 6.12 (2H,s); ca. 6.9 (1H,d); 7.5 (1H,broad,s); ca. 7.7 (1H,broad d)

GLC retention time:1.87 minutes

4-Trifluoromethoxy-α,α,α-trifluoroacetophenone, from 4-bromotrifluoromethoxybenzene.

4-Bromotrifluoromethoxybenzene may be prepared from trifluoromethoxybenzene by the process described in the Journal of Organic Chemistry, 29, 1, (1964).

Boiling point:164°–166° C. (atmosphere pressure).

$^1$H NMR (CDCl$_3$)δ (ppm):7.35, 8.14 (4H,d)

$^{19}$F NMR (CDCl$_3$)δ (ppm relative to CFCl$_3$):−58.1 (s) CF$_3$O; −72.1 (s) CF$_3$ GLC retention time:1.50 minutes (50° C.–280° C. run)

EXAMPLE 3

This Example illustrates the preparation of 4-ethoxy-α,α,α-trifluoroacetophenone.

A. From trifluoroacetic acid.

Literature reference: Journal of Organic Chemistry, 32, 1311, (1967).

A solution of 4-bromo-ethoxybenzene (60 g) in diethyl ether (100 cm³) was added slowly to a stirred mixture of magnesium turnings (7.4 g), diethyl ether (50 cm³) and a crystal of iodine (ca. 0.5 g) under a nitrogen atmosphere. After ca. 15 cm³ of the solution had been added the mixture was warmed gently until the reaction commenced and the rate of addition was thereafter adjusted to maintain a gentle reflux. After the completion of the addition (ca. 30 minutes) the mixture was stirred for a further 20 minutes at the ambient temperature (ca. 22° C.), following which a solution of trifluoroacetic acid (12.0 g) in diethyl ether (25 cm³) was added dropwise over a period of one hour. The mixture was then heated at the reflux temperature for a further one hour after which the mixture was poured into crushed ice and acidified with concentrated hydrochloric acid. The organic layer was separated, and the aqueous layer extracted three times with diethyl ether and the extracts combined with the organic layer, and the ethereal solution washed twice with saturated sodium bicarbonate, and dried over anhydrous sodium sulphate. After removal of the solvent by evaporation under reduced pressure the residual oil (48 g) was subjected to fractional distillation. Three fractions were collected at 64° C./0.1–0.2 mg Hg, containing 1.2 g (75% pure by gas-liquid chromatography), 13 g (91% pure) and 2.4 g (85% pure) of 4-ethoxytrifluoroacetophenone respectively. The major fraction was used without further purification.

$^1$H NMR (CDCl$_3$)δ:1.46 (3H,t); 4.15 (2H,q); 7.0 (2H,m); 8.05 (2H,m).

Infra red (liquid film):1710 cm$^{-1}$.

B. From trifluoroacetic anhydride.

A solution of 4-bromoethoxybenzene (150 g) in diethyl ether (200 cm³) was added slowly to a stirred mixture of magnesium turnings (20.0 g), diethyl ether (50 cm³) and a crystal of iodine (ca. 0.5 g) under a nitrogen atmosphere. After ca. 35 cm³ of the solution had been added the mixture was warmed gently until the reaction commenced and the rate of addition was adjusted to maintain a gentle reflux. After the addition was complete the mixture was stirred for a further one hour at the ambient temperature (ca. 22° C.) after which the mixture was cooled at 0° C. by external cooling and a solution of trifluoroacetic anhydride (203 g) in diethyl ether (100 cm³) was added, initially drop by drop, and then at a faster rate so as to maintain a gentle reflux. The addition was completed over a period of 20 minutes after which the mixture was stirred for a further 45 minutes. The mixture was then poured onto crushed ice and the product worked up in the manner set out in part A above, to give, after distillation, 4-ethoxytrifluoroacetophenone (35 g).

EXAMPLE 4

By the use of procedures similar to those set out in parts A and B of Example 3 above, the following compounds were prepared from the appropriate starting material.

(i) 4-Methoxy-α,α,α-trifluoroacetophenone, from 4-bromomethoxybenzene and trifluoroacetic anhydride.

$^1$H NMR (CDCl$_3$)δ (ppm):3.90 (3H,s); 7.02 (2H,d); 8.05 (2H,d)

GLC retention time:3.75 minutes (50° C.–280° C. run)

(ii) 4-t-Butyl-α,α,α-trifluoroacetophenone, from 4-bromo-t-butylbenzene and trifluoroacetic anhydride.

GLC retention time:1.83 minutes (iii) 4-Trifluoromethoxy-α,α,α-trifluoroacetophenone, from 4-bromotrifluoromethoxybenzene and trifluoroacetic anhydride.

In this case, the product was purified by distillation in a Kugelrohr apparatus, under reduced pressure (ca. 12 mm Hg), at an oven temperature of 50°–70° C.

$^1$H NMR (CDCl$_3$)δ (ppm):7.35, 8.14 (4H,d)

$^{19}$F NMR (CDCl$_3$):(ppm-relative to CFCl$_3$):−58.1 (CF$_3$O, S); −72.1 (CF$_3$, S)

IR:1730, 1610, 1270, 1150–1250 cm.$^{-1}$ (iv) 4-Chloro-α,α,α-trifluoroacetophenone, from 4-bromochlorobenzene and trifluoroacetic anhydride.

$^1$H NMR (CDCl$_3$)δ (ppm):ca. 7.6, 8.1 (each 2H, ABq)

GLC retention time:2.56 minute (50° C.–280° C. run)

EXAMPLE 5

This Example illustrates the preparation of 4-methyl-α,α,α-trifluoroacetophenone.

Literature reference: Tetrahedron, 42, 547, (1986)

A stirred mixture of aluminium chloride (8.33 g) toluene (20 cm$^3$) and carbon disulphide (10 cm$^3$) was cooled to −40° C. (±5° C). Trifluoroacetyl chloride (6.92 g) was condensed into the reaction vessel from a cylinder and the reaction mixture was stirred at −40° for 3 hours. The mixture was carefully poured into a mixture of ice and concentrated hydrochloric acid; caution was necessary during the quenching in view of the observed exothermic reaction. The organic layer was separated and the aqueous layer extracted with diethyl ether (3×100 cm$^3$). The combined organic layers were washed with saturated sodium carbonate solution, then water, and finally dried over anhydrous sodium sulphate to give a pale yellow solution.

Removal of the solvent by distillation at atmospheric pressure gave an oil, which was shown by gas liquid chromatography to consist of a mixture of toluene and the required product, 4-methyl-α,α,α-trifluoroacetophenone. The product was purified by distillation, and identified as the required product by gas liquid chromatographic comparison with an authentic sample.

GLC retention time: 2.37 minutes (50° C.–280° C. run)

EXAMPLE 6

By use of a procedure similar to that described in Example 5 above, the following compound was prepared from the appropriate starting material.

(i) 4-n-Propyl-α,α,α-trifluoroacetophenone from 4-bromo-n-propylbenzene.

$^1$H NMR (CDCl$_3$)δ (ppm):0.95 (3H,t); ca. 1.68 (2H,m); 2.7 (2H,t); 7.35 (2H,d); 8.0 (2H,d).

EXAMPLE 7

This Example illustrates the preparation of 1,1,1-trifluoro-2-(4-ethoxyphenyl)prop-2-ene oxide.

Trimethylsulphoxonium iodide (8.1 g) was added to a stirred solution of 4-ethoxy-α,α,α-trifluoroacetophenone (8 g) in t-butanol (25 cm$^3$). When the addition was complete, Potassium hydroxide pellets (2 g) were added, and the reaction mixture was heated at the reflux temperature for one hour. The mixture was cooled, and poured into a dilute aqueous solution of hydrochloric acid. The aqueous mixture was extracted eight times with diethyl ether and the combined extracts were dried over anhydrous magnesium sulphate. Removal of the solvent by evaporation under reduced pressure gave a pale yellow oil (5.5 g) containing a small amount of solid residue. The crude product residue was passed through a plug of silica gel, using n-hexane containing 10% by volume ethyl acetate as eluent. Further purification by chromatography using a silica gel column eluted with n-hexane containing 10% by volume ethyl acetate gave two fractions containing 1,1,1-trifluoro-2-(4-ethoxyphenyl)prop-2-ene oxide. The first fraction was shown by gas liquid chromatography to be 79% pure, the second 98% pure.

$^1$H NMR (CDCl$_3$)δ (ppm):1.42 (3H,t); 2.9 (1H,dq); 3.38 (1H,d); 4.07 (2H,q); 6.9, 7.4 (4H,m).

EXAMPLE 8

By use of a procedure similar to that described in Example 7 above, the following compounds were prepared from the appropriate starting materials.

(i) 1,1-Trifluoro-2-(4-methylphenyl)prop-2-ene oxide, from 4-methyl-α,α,α-trifluoroacetophenone $^1$H NMR (CDCl$_3$)δ (ppm):2.4 (3H,s); ca. 2.9 (1H,dq); ca. 3.4 (1H,d); ca. 7.3 (4H,ABq)

GLC retention time:3.02 minutes (50° C.–280° C. run)

(ii) 1,1,1-Trifluoro-2-(4-ethoxy-3-fluorophenyl)prop-2-ene oxide, and 1,1,1-trifluoro-2-(4-ethoxy-3-fluorophenyl)propan-2,3-diol from 4-ethoxy-3-fluoro-α,α,α-trifluoro-acetophenone.

In this case, the reaction mixture was heated at the reflux temperature for 3 hours, under an atmosphere of nitrogen. Analysis of the reaction mixture by gas liquid chromatography showed 2 major products. The first product was identified as the expected epoxide, and was purified by distillation in a Kugelrohr apparatus, under reduced pressure (ca. 20 mmHg), at an oven temperature of 120° C., to give the epoxide in 85% purity:

$^1$H NMR (CDCl$_3$)δ (ppm):1.45 (3H,t); 2.92 (1H,m); 3.4 (1H,m); 4.12 (2H,q); 6.95 (1H,t); 7.2–7.3 (2H,m)

The second product was Purified by further distillation under high vacuum (0.1 mmHg) at an oven temperature of 130° C., and identified as 1,1,1-trifluoro-2-(4-ethoxy-3-fluorophenyl)propan-2,3-diol (85% pure).

$^1$H NMR (CDCl$_3$)δ (ppm):1.45 (3H,t); 1.9 (1H, broad); 3.5–4.5 (5H,m-incorporating 1H broad, 2H,m and 2H,q); 6.9–7.5 (3H,m)

(iii) 1,1,1-Trifluoro-2-(4-t-butylphenyl)prop-2-ene oxide, from 4-t-butyl-α,α,α-trifluoroacetophenone.

In this case, the product was obtained in 50% purity, shown by gas liquid chromatography to be mixed primarily with unreacted starting ketone. The product was used without further purification.

$^1$H NMR (CDCl$_3$)δ (ppm):1.4 (9H,s); 2.9 (1H,m); 3.4 (1H,broad d); 7.5 (4H,m); other signals due to starting material also recorded GLC retention time: 2.21 minutes (GLC retention time of starting ketone: 1.73 minutes).

(iv) 1,1,1-Trifluoro-2-(4-n-propylphenyl)prop-2-ene oxide, from 4-n-propyl-α,α,α-trifluoroacetophenone.

$^1$H NMR (CDCl$_3$)δ (ppm): 0.9 (3H,t); ca. 1.6 (2H, m); 2.58 (2H,t); ca. 2.9 (1H,m); 3.4 (1H,d); 7.1–7.5 (4H,ABq)

GLC retention time: 2.06 minutes (v) 1,1,1-Trifluoro-2-(5-indanyl)prop-2-ene oxide, from 5-trifluoroacetylindane.

$^1$H NMR (CDCl$_3$)δ (ppm): 2.1 (2H, m), 2.9 (5H,m); 3.4 (1H,d); 7.26 (2H, ABq); 7.38 (1H,s).

$^{19}$F NMR (CDCl$_3$)δ (ppm - relative to CFCl$_3$): −75.1 (CF$_3$, S).

GLC retention time: 2.61 minutes.

(vi) 1,1,1-Trifluoro-2-(4-fluorophenyl)-prop-2-ene oxide, from 4-fluoro-α,α,α-trifluoroacetophenone.

$^1$H NMR (CDCl$_3$)δ (ppm): 2.9 (1H,m); 3.4 (1H,d); 7.0-7.6 (4H,m).

$^{19}$F NMR (CDCl$_3$)δ (ppm - relative to CFCl$_3$): 75.2 (CF$_3$,S); −111.7 (1F,m).

GLC retention time: 2.18 minutes (50° C.-280° C. run)

(vii) 1,1,1-Trifluoro-2-(4-chlorophenyl)prop-2-ene oxide, from 4-chloro-α,α,α-trifluoroacetophenone.

$^1$H NMR (CDCl$_3$)δ (ppm): 2.9 (1H,m ; 3.42 (1H,d); 7.2-7.6 (4H,m)

$^{19}$F NMR (CDCl$_3$)δ (ppm) - relative to CFCl$_3$) −75.0 (CF$_3$, S).

GLC retention time: 1.42 minutes (3.59 minutes for 50° C.-280° C. run).

EXAMPLE 9

This Example illustrates the preparation of 1,1,1-trifluoro-2-(4-ethoxyphenyl)-3-(3-phenoxybenzyloxy) propan-2-ol.

A mixture of 3-phenoxybenzyl alcohol (0.84 g) and sodium hydride (0.25 g - prepared by washing 0.5 g of a 50% dispersion in oil with petroleum ether of boiling range 60°-80° C. under an atmosphere of nitrogen) in dry N,N-dimethyl-formamide (15 cm$^3$) was stirred at the ambient temperature (ca. 22° C.) until evolution of hydrogen had ceased (30 minutes). A solution of 1,1,1-trifluoro-2-(4-ethoxyphenyl)prop-2-ene oxide (1g) in N,N-dimethylformamide (5 cm$^3$) was then added to the stirred mixture. After one hour, analysis by gas liquid chromatography indicated that no starting materials remained in the reaction mixture. The mixture was quenched with water and extracted three times with ethyl acetate. The combined extracts were dried over anhydrous sodium sulphate, and concentrated by evaporation of the solvent under reduced pressure. The residual, pale yellow oil was purified by flash column chromatography on a silica gel support, using n-hexane containing 15% by volume ethyl acetate as eluent, to give 1,1,1-trifluoro-2-(4-ethoxyphenyl)-3-(3-phenoxybenzyloxy)propan-2-ol (1.85 g) as a colourless oil.

$^1$H NMR (CDCl$_3$) δ (ppm): 1.44 (3H,t); 3.65 (1H,s); 3.67 (1H,d); 4.0-4.2 (3H,m); 4.6 (2H,s); 6.8-7.5 (13H,m)

The signal at 3.65 disappeared on shaking the sample will D$_2$O, revealing the signal at 3.67.

$^{19}$F NMR δ (ppm - relative to CFCl$_3$): −77.9 (CF$_3$)

IR (liquid film): 3540, 1620, 1592, 1520, 1493, 1260, 1170 cm$^{-1}$

GLC retention time: 11.90 minutes.

EXAMPLE 10

By the use of a procedure similar to that illustrated in Example 9 above, the following compounds were prepared from the appropriate starting materials.

(i) 1,1,1-Trifluoro-2-(4-ethoxyphenyl)-3-(4-fluoro-3-phenoxybenzyloxy)propan-2-ol, from 1,1,1-trifluoro-2-(4-ethoxyphenyl)prop-2-ene oxide and 4-fluoro-3-phenoxybenzyl alcohol.

$^1$H NMR (CDCl$_3$) δ (ppm): 1.41 (3H,t); 3.6 (1H,s); 3.63 (1H,d - small coupling to CF$_3$); 4.02 (2H,q); 4.04 (1H,d); 4.62 (2H,s); 6.8-7.5 (12H,m)

$^{19}$F NMR (CDCl$_3$) δ (ppm - relative to CFCl$_3$): −77.9 (3F); −132.18 (1F,m)

IR (liquid film): 3540, 1613, 1591, 1514, 1427, 1282, 1254, 1210, 1180, 1166 cm$^{31\ 1}$ GLC retention time: 11.85 minutes (ii) 1,1,1-Trifluoro-2-(4-ethoxyphenyl)-3-(4-methyl-2,3,5,6-tetrafluorobenzyloxy)propan-2-ol from 1,1,1-trifluoro-2-(4-ethoxyphenyl)prop-2-ene oxide and 4-methyl-2,3,5,6-tetrafluorobenzyl alcohol.

$^1$H NMR (CDCl$_3$) δ (ppm): 1.41 (3H,t); 2.27 (3H,t); 3.55 (1H,s); ca. 3.7 (1H,broad d); 4.04 (2H,q); 4.12 (1H,d); 4.7 (2H,ABq); 6.9-7.4 (4H,m)

$^{19}$F NMR (CDCl$_3$) δ (ppm - relative to CFCl$_3$): −78 (3F); −143.6-145.8 (4F,m)

IR (liquid film): 3550 cm$^{-1}$ (OH)

GLC retention time: 8.31 minutes.

(iii) 1,1,1-Trifluoro-2-(4-methylphenyl)-3-(3-phenoxybenzyloxy)propan-2-ol, from 1,1,1-trifluoro-2-(4-methylphenyl)prop-2-ene oxide and 3-phenoxybenzyl alcohol.

$^1$H NMR (CDCl$_3$) δ (ppm): 2.33 (3H,s); 3.66 (1H,d); 3.76 (1H,s); 4.08 (1H,d); 4.56 (2H,s); 6.9-7.4 (13H,m).

GLC retention time: 10.76 minutes.

(iv) 1,1,1-Trifluoro-2-(3-fluoro-4-ethoxyphenyl)-3-(3-(4-chlorophenoxy)benzyloxy) propan-2-ol, from 1,1,1-trifluoro-2-(3-fluoro-4-ethoxyphenyl)prop-2-ene oxide and 3-(4-chlorophenoxy)benzyl alcohol.

$^1$H NMR (CDCl$_3$) δ (ppm): 1.46 (3H,t); 3.64 (1H,d); 3.65 (1H,s); 4.04 (1H,d); 4.1 (2H,q); 4.57 (2H,ABq); 6.9-7.35 (11H,m).

GLC retention time: 12.68 minutes.

(v) 1,1,1-Trifluoro-2-(4-t-butylphenyl)-3-(3-phenoxy-4-fluorobenzyloxy)propan-2-ol, from 1,1,1-trifluoro-2-(4-t-butylphenyl)prop-2-ene oxide and 3-phenoxy-4-fluorobenzyl alcohol.

In this case the epoxide starting material used was that prepared in Example 8 (iii) above, and was contaminated with ca. 40% unreacted 4-t-butyl-α,α,α-trifluoroacetophenone. The acetophenone was, surprisingly, found to react with the alcohol in preference to the epoxide. It was therefore necessary to isolate the unreacted epoxide and repeat the reaction in the absence of acetophenone.

$^1$H NMR (CDCl$_3$) δ (ppm): 1.3 (9H,s); 3.62 (1H,s); 3.64 (1H,broad d); 4.08 (1H,d); 4.52 (2H,s); 7.0-7.5 (12H,m).

$^{19}$F NMR (CDCl$_3$) δ (ppm - relative to CFCl$_3$): −77.5 (CF$_3$-S); −132.1 (1F,m).

GLC retention time: 11.78 minutes.

(vi) 1,1,1-Trifluoro-2-(4-n-propylphenyl)-3-(3-phenoxy-4-fluorobenzyloxy)propan-2-ol, from 1,1,1-trifluoro-2-(4-n-propylphenyl)prop-2-ene oxide and 3-phenoxy-4-fluorobenzyl alcohol.

$^1$H NMR (CDCl$_3$) δ (ppm): 0.93 (3H,t); ca. 1.6 (2H,m); 2.6 (2H,t); 3.64 (1H,d); overlapping with 3.62 (1H,s); 4.08 (1H,d); 4.5 (2H,s); 6.9-7.4 (12H,m).

$^{19}$F NMR (CDCl$_3$) δ (ppm - relative to CFCl$_3$): −77.6 (CF$_3$,s); −132.1 (1F,m).

GLC retention time: 11.66 minutes (vii) 1,1,1-trifluoro-2-(5-indanyl)-3-(3-phenoxy-4-fluorobenzyloxy)propan-2-ol, from 1,1,1-trifluoro-2-(5-indanyl)prop-2-ene oxide and 3-phenoxy-4-fluorobenzyl alcohol.

$^1$H NMR (CDCl$_3$) δ (ppm): 2.08 (2H,m); 2.90 (4H,m); 3.64 (1H,d); 3.63 (1H,s); 4.08 (1H,d); 4.55 (2H,s); 6.95–7.4 (11H,m).

GLC retention time: 12.18 minutes.

(viii) 1,1,1-Trifluoro-2-(4-fluorophenyl)-3-(3-phenoxy-4-fluorobenzyloxy)propan-2-ol, from 1,1,1-trifluoro-2-(4-fluorophenyl)prop-2-ene oxide and 3-phenoxy-4-fluorobenzyl alcohol.

$^1$H NMR (CDCl$_3$) δ (ppm): 3.62 (1H,d); overlapping with 3.65 (1H,s); 4.06 (1H,d); 4.52 (2H,s): 6.9–7.5 (12H,m).

GLC retention time: 10.6 minutes.

(ix) 1,1,1-Trifluoro-2-(4-chlorophenyl)-3-(3-phenoxy-4-fluorobenzyloxy)propan-2-ol, from 1,1,1-trifluoro-2-(4-chlorophenyl)prop-2-ene oxide and 3-phenoxy-4-fluorobenzyl alcohol.

$^1$H NMR (CDCl$_3$) δ (ppm): 3.62 (1H,d); overlapping with 3.64 (1H,s); 4.03 (1H,d); 4.52 (2H,s); 6.9–7.5 (12H,m).

$^{19}$F NMR (CDCl$_3$) δ (ppm - relative to CFCl$_3$): −77.7 (CF$_3$, s).

GLC retention time: 11.16 minutes.

(x) 1,1,1-Trifluoro-2-(4-bromophenyl)-3-(3-phenoxy-4-fluorobenzyloxy)propan-2-ol, from 1,1,1-trifluoro-2-(4-bromophenyl)prop-2-ene oxide and 3-phenoxy-4-fluorobenzyl alcohol.

$^1$H NMR (CDCl$_3$) δ (ppm): 3.62 (1H,d); 3.67 (1H,s); 4.02 (1yh,d); 4.50 (2H,s); 6.9–7.5 (12H,m).

GLC retention time: 11.7 minutes.

(xi) 1,1,1-Trifluoro-2-(4-ethoxyphenyl)-3-(3-(4-chlorophenoxy)benzyloxy)propan-2-ol, from 1,1,1-trifluoro-2-(4-ethoxyphenyl)prop-2-ene oxide and 3-(4-chlorophenoxy)benzyl alcohol.

$^1$H NMR (CDCl$_3$) δ (ppm): 1.42 (3H,t); 3.63 (1H,s); 3.66 (1H,d); ca. 4.0 (2H,q); overlapping with (1H,d); 4.58 (2H,ABq); 6.3–7.5 (12H,m).

$^{19}$F NMR CDCl$_3$) δ (ppm - relative to CFCl$_3$): −77.9 (CF$_3$,S).

GLC retention time: 13.07 minutes.

(xii) 1,1,1-Trifluoro-2-(4-ethoxyphenyl)-3-(3-(4-bromophenoxy)-4-fluorobenzyloxy) propan-2-ol, from 1,1,1-trifluoro-2-(4-ethoxyphenyl)prop-2-ene oxide and 3-(4-bromophenoxy)-4-fluorobenzyl alcohol.

The preparation of 3-(4-bromophenoxy)-4-fluorobenzyl alcohol is described in Example 38.

$^1$H NMR (CDCl$_3$) δ (ppm): 1.42 (3H,t); 3.60 (1H,s); 3.65 (1H,d); 4.02 (2H,q); overlapping with 4.04 (1H,d); 4.52 (2H,s); 6.8–7.5 (11H,m). $^{19}$F NMR (CDCl$_3$) δ (ppm - relative to CFCl$_3$): −77.8 (CF$_3$,s) −131.7 (1F,m).

GLC retention time: 13.41 minutes.

(xiii) 1,1,1-Trifluoro-2-(4-ethoxyphenyl)-3-(3-(4-chlorophenoxy)-4-fluorobenzyloxy) propan-2-ol, from 1,1,1-trifluoro-2-(4-ethoxyphenyl)prop-2-ene oxide and 3-(4-chlorophenoxy)-4-fluorobenzyl alcohol.

The preparation of 3-(4-chlorophenoxy)-4-fluorobenzyl alcohol is described in Example 39.

$^1$H NMR (CDCl$_3$) δ (ppm): 1.43 (3H,t); 3.6 (1H,s); 3.65 (1H,d); 4.04 (2H,q); overlapping with (1H,d); 4.52 (2H,s ; 6.8–7.4 (11H,m).

$^{19}$F NMR (CDCl$_3$) δ (ppm - relative to CFCl$_3$): −77.8 (CF$_3$,s) −131.8 (1F,m).

GLC retention time: 12.78 minutes.

(xiv) 1,1,1-Trifluoro-2-(4-ethoxyphenyl)-3-(5-benzyl-3-furanylmethyloxy)-propan-2-ol, from 1,1,1-trifluoro-2-(4-ethoxyphenyl)prop-2-ene oxide and 5-benzyl-3-hydroxymethylfuran.

$^1$H NMR (CDCl$_3$) δ (ppm): 1.41 (3H,t ; 3.65 (1H,s); overlapping with 3.63 (1H,d); 3.95 (2H,s); 4.0–4.1 (2H,q) overlapping with (1H,d); 4.2 (2H,s); 6.0 (1H,s); 6.9 (2H,d); 7.2–7.4 (8H,m)

$^{19}$F NMR (CDCl$_3$) δ (ppm - relative to CFCl$_3$): −78.0 (CF$_3$,s).

GLC retention time: 11.37 minutes.

(xv) 1,1,1-Trifluoro-2-(4-ethoxyphenyl)-3-(3-benzyl-4-fluorobenzyloxy)propan-2-ol, from 1,1,1-trifluoro-2-(4-ethoxyphenyl)prop-2-ene oxide and 3-benzyl-4-fluorobenzyl alcohol.

The preparation of 3-benzyl-4-fluorobenzyl alcohol is described in Example 40.

$^1$H NMR (CDCl$_3$) δ (ppm): 1.4 (3H,t ; 3.6 (2H,s); 4.0 (4H,m); 4.5 (2H,s); 7.4–6.8 (12H,m).

$^{19}$F NMR (CDCl ) δ (ppm - relative to (CFCl$_3$): −77.9 (CF$_3$,s); −119.0 (1F,m)

IR (liquid film): 3600–3300 cm$^{-1}$ (OH)

EXAMPLE 11

This Example illustrates the preparation of 1,1,1-trifluoro-2-(4-bromophenyl)prop-2-ene oxide.

Trimethylsulphoxonium iodide (2.2 g) was added gradually to a stirred suspension of sodium hydride (0.25 g - prepared by washing 0.5 g of a 50% dispersion in oil with petroleum ether of boiling range 60°–80° C. under an atmosphere of nitrogen) in dry N,N-dimethylformamide (10 cm$^3$). After evolution of hydrogen had ceased, a solution of 4-bromo-α,α,α-trifluoroacetophenone (2.53 g) in dry N,N-dimethyl-formamide (10 cm$^3$) was added to the reaction mixture. A solid precipitate was redissolved by the addition of further N,N-dimethylformamide (10 cm$^3$), and the mixture was stirred at the ambient temperature (ca. 22° C.) for a further one hour. After cautious addition of water, the reaction mixture was poured onto ice, and the aqueous mixture extracted three times with diethyl ether. The combined extracts were dried over anhydrous magnesium sulphate and concentrated by evaporation of the solvent under reduced pressure. The residual yellow oil (2.1 g) was purified by filtration through silica gel, using diethyl ether as eluent. The major product-containing fraction was concentrated by evaporation of the eluent under reduced pressure, and purified by distillation of the residual oil (1.4 g) in a Kugelrohr apparatus, under reduced pressure (20–30 mmHg), at an oven temperature of 150° C. to give 1,1,1-trifluoro-2-(4-bromophenyl)prop-2-ene oxide (0.785 g) as a colourless oil.

$^1$H NMR (CDCl$_3$) δ (ppm): 2.9 (1H,m - probably dq); 3.4 (1H,d); 7.3–7.6 (4H,aromatic m).

NB. The propene oxides prepared by the method of this Example need not be isolated but may be used directly as formed, in solution in N,N-dimethylformamide, for reaction with alcohols as described in Example 12.

EXAMPLE 12

This Example illustrates the two stage preparation of 1,1,1-trifluoro-2-(3,4-methylenedioxyphenyl)-3-(3-phenoxybenzyloxy)propan-2-ol.

Stage 1: Preparation of 1,1,1-trifluoro-2-(3,4-methylenedioxyphenyl)prop-2-ene oxide.

Sodium hydride (0.22 g, in the form of 0.44 g of a 50% dispersion in oil) was added to a stirred suspension of trimethylsulphoxonium iodide (2 g) in dry N,N-dimethylformamide (50 cm$^3$) at the ambienet temperature (ca. 22° C.) and under an atmosphere of nitrogen. When evolution of hydrogen had ceased, 3,4-methylenedioxy-α,α,α-trifluoroacetophenone (2 g) was added to the reaction mixture. After 5 minutes, analysis of the reaction mixture by gas liquid chromatography showed a major signal at a retention time of 2.26 minutes corresponding to 1,1,1-trifluoro-2-(3,4-methylenedioxy)prop-2-ene oxide, but no trace of the ketone starting material (expected retention time 1.87 minutes). The solution of the epoxide was used immediately in stage 2 of the reaction.

Stage 2:

3-Phenoxybenzyl alcohol (1.0 g) was added to a stirred suspension of sodium hydride (0.22 g, in the form of 0.44 g of a 50% dispersion in oil) in dry N,N-dimethylformamide (40 cm$^3$), under an atmosphere of nitrogen. The mixture was stirred for a further 2 hours, during which time evolution of hydrogen occurred, and then added dropwise to the epoxide solution prepared in Stage 1. After a further 2 hours stirring at the ambient temperature (ca. 22° C.), the reaction mixture was poured into water, and the aqueous mixture acidified with dilute hydrochloric acid. This mixture was extracted with diethyl ether and the organic layer washed with water, dried over anhydrous magnesium sulphate, and concentrated by evaporation under reduced pressure to give an oil. The oil was purified by column chromatography on a silica gel support, eluting with n-hexane containing 15% by volume ethyl acetate, to give 1,1,1-trifluoro-2-(3,4-methylenedioxyphenyl)-3-(3-phenoxybenzyloxy)propan-2-ol (1.83 g), as a colourless oil.

$^1$H NMR (CDCl$_3$) δ (ppm): 3.62 (1H,d); 3.68 (1H,s); 4.04 (1H,d); 4.57 (2H,s); 5.96 (2H,s); 5.8–7.4 (12H,m).

$^{19}$F NMR (CDCl$_3$) δ (ppm - relative to CFCl$_3$) −77.8 (CF$_3$, S).

EXAMPLE 13

By use of the two stage procedure described in Example 12, the following compounds were prepared from the appropriate starting material.

(i) 1,1,1-Trifluoro-2-(3,4-methylenedioxyphenyl)-3-(3-(4-chlorophenoxy)benzyloxy)propan-2-ol, from 3,4-methylenedioxy-α,α,α-trifluoroacetophenone and 3-(4-chlorophenoxy)benzyl alcohol.

$^1$H NMR (CDCl$_3$) δ (ppm): 3.62 (1H,d); 3.65 (1H,s); 4.03 (1H,d); 4.58 (2H,s); 5.98 (2H,s); 6.8–7.4 (11H,m).
GLC retention time: 13.09 minutes.

(ii) 1,1,1-Trifluoro-2-(4-methoxyphenyl)-3-(3-phenoxybenzyloxy)propan-2-ol, from 4-methoxy-α,α,α-trifluoroactophenone and 3-phenoxybenzyl alcohol.

$^1$H NMR (CDCl$_3$) δ (ppm): 3.66 (1H,d with extra fine coupling); 3.72 (1H,s); 3.76 (3H,s); 4.05 (1H,d); 4.55 (2H, ABq); 6.8–7.5 (13H,m).
GLC retention time: 11.54 minutes.

(iii) 1,1,1-Trifluoro-2-(4-methoxyphenyl)-3-(3-phenoxy-4-fluorobenzyloxy)propan-2-ol, from 4-methoxy-α,α,α-trifluoroacetophenone and 3-phenoxy-4-fluorobenzyl alcohol.

$^1$H NMR (CDCl$_3$) δ (ppm): 3.62 (1H,s); 3.64 (1H,d); 3.76 (3H,s); 4.05 (1H,d); 4.50 (2H,s); 6.8–7.5 (12H,m)
GLC retention time: 10.77 minutes.

(iv) 1,1,1-Trifluoro-2-(4-methoxymethylphenyl)-3-(3-(4-chlorophenoxy)benzyloxy)propan-2-ol, from 4-methoxymethyl-α,α,α-trifluoroacetophenone and 3-(4-chlorophenoxy)benzyl alcohol.

$^1$H NMR (CDCl$_3$) δ (ppm): 3.4 (3H,s); 3.65 (1H,d); 3.7 (1H,s); 4.12 (1H,d); 4.45 (2H,s); 4.57 (1H,s); 6.9–7.5 (12H,m).
GLC retention time: 12.79 minutes (GLC retention time of intermediate epoxide: 2.17 minutes).

(v) 1,1,1-Trifluoro-2-(4-methoxymethylphenyl)-3-(3-phenoxybenzyloxy)propan-2-ol, from 4-methoxymethyl-α,α,α-trifluoroacet ophenone and 3-phenoxybenzyl alcohol.

$^1$H NMR (CDCl$_3$) δ (ppm): 3.39 (3H,s); 3.66 (1H,d); 3.7 (1H,s); 4.12 (1H,d); 4.45 (2H,s); 4.58 (2H,s); 6.9–7.55 (13H,m)
GLC retention time: 11.76 minutes (vi) 1,1,1-Trifluoro-2-(4-trifluoromethoxyphenyl)-3-(3-phenoxy-4-fluorobenzyloxy)propan-2-ol, from 4-trifluoromethoxy-α,α,α-trifluoroacetophenone and 3-phenoxy-4-fluorobenzyl alcohol.

$^1$H NMR (CDCl$_3$) δ (ppm): 3.61 (1H,d); 3.65 (1H,s); 4.03 (1H,d); 4.5 (2H,s); 6.9–7.6 (12H,m).

$^{19}$F NMR (CDCl$_3$) δ (ppm - relative to (CFCl$_3$): −58.3 (CF$_3$O, s); −77.6 (CF$_3$,s); −131.8 (1F,m)
GLC retention time: 9.88 minutes
(GLC retention time of intermediate epoxide: 2.34 minutes −50° C.–280° C. run)

(vii) 1,1,1-Trifluoro-2-(4-trifluoromethoxyphenyl)-3-(3-(4-chlorophenoxy)benzyloxy)propan-2-ol, from 4-trifluoromethoxy-α,α,α-trifluoroacetophenone and 3-(4-chlorophenoxy)benzyl alcohol.

$^1$H NMR (CDCl$_3$) δ (ppm): 3.65 (1H,d); 3.73 (1H,s); 4.1 (1H,d); 4.57 (2H,ABq); 6 9–7.6 (12H,m).

$^{19}$F NMR (CDCl$_3$) δ (ppm - relative to CFCl$_3$): −58.3 (CF$_3$,s); −77.7 (CF$_3$,s)
GLC retention time: 11.06 minutes (viii) 1,1,1-Trifluoro-2-(4-trifluoromethylphenyl)-3-(3-phenoxybenzyloxy)propan-2-ol, from 4-trifluoromethyl-α,α,α-trifluoroacetophenone and 3-phenoxybenzyl alcohol.

$^1$H NMR (CDCl$_3$) δ (ppm): 3.68 (1H,d); 3.78 (1H,s); 4.1 (1H,d); 4.58 (2H,ABq); 6.8–7.4 (9H,m); 7.63 (4H,s)

$^{19}$F NMR (CDCl$_3$) δ (ppm - relative to (CFCl$_3$): −63.3 (CF$_3$,s); −77.5 (CF$_3$,s)
GLC retention time: 9.88 minutes
(GLC retention time of intermediate epoxide: 2.27 minutes)

(ix) 1,1,1-Trifluoro-2-(4-trifluoromethylphenyl)-3-(3-phenoxy-4-fluorobenzyloxy)propan-2-ol, from 4-trifluoromethyl-α,α,α-trifluoroacetophenone and 3-phenoxy-4-fluorobenzyl alcohol.

$^1$H NMR (CDCl$_3$) δ (ppm): 3.65 (1H,d ; 3.72 (1H,s); 4.08 (1H,d); 4.52 (2H,s); 6.9–7.4 (8H,m); 7.6 (4H,s).

$^{19}$F NMR (CDCl$_3$) δ (ppm - relative to (CFCl$_3$): −63.3 (CF$_3$,s); −77.5 (CF$_3$,s); −131.8 (1F,m).
GLC retention time: 9.88 minutes (x) 1,1,1-Trifluoro-2-(4-trifluoromethoxyphenyl)-3-(6-phenoxy-2-pyridylmethyloxy)propan-2-ol, from 4-trifluoromethoxy-α,α,α-trifluoroacetophenone and 6-phenoxy-2-hydroxymethylpyridine.

$^1$H NMR (CDCl$_3$) δ (ppm): 3.89 (1H,d); 4.22 (1H,d); 4.64 (2H,ABq); ca. 5.4 (1H,broad s); 6.7–7.7 (12H,m).

$^{19}$F NMR (CDCl$_3$) δ (ppm relative to CFCl$_3$): −58.3 (CF$_3$,s); −77.7 (3F,s).
GLC retention time: 9.82 minutes

EXAMPLE 14

This Example illustrates the preparation of 1,1,1-trifluoro-2-(4-trifluoromethoxyphenyl)propan-2,3-diol.

A mixture of 4-trifluoromethoxy-α,α,α-trifluoroacetophenone (4 g), trimethylsulphoxonium iodide (3.4 g) and potassium hydroxide pellets (0.85 g) in t-butanol (20 cm$^3$) was heated at the reflux temperature for two hours. After cooling, the reaction mixture was poured into water, and the aqueous mixture extracted with diethyl ether. The combined extracts were washed twice with water, dried over anhydrous magnesium sulphate and concentrated by evaporation of the solvent under reduced pressure The residual oil (4.1 g) was purified by distillation in a Kugelrohr apparatus, under reduced pressure (0.2 mmHg), at an oven temperature of 110°–130° C. The purified oil (1.3 g) was identified as 1,1,1-trifluoro-2-(4-trifluoromethoxyphenyl)-propan-2,3-diol, rather than the expected epoxide.

$^1$H NMR (CDCl$_3$) δ (ppm): 2.5 (1H,broad); 3.9, 4.3 (1H,d); 4.1 (1H,broad); 7.2–7.6 (4H,q)

The signals at 2.5 and 4.1 disappeared on shaking the sample with D$_2$O.

IR (liquid film): 3430 cm$^{-1}$ (OH)

EXAMPLE 15

This Example illustrates the preparation of 1,1,1-trifluoro-2-(4-trifluoromethoxyphenyl)-3-(3-phenoxybenzyloxy)-propan-2-ol.

1,1,1-Trifluoro-2-(4-trifluoromethoxyphenyl)propan-2,3-diol (0.6 g), prepared as described in Example 14, 3-phenoxybenzyl bromide (0.54 g), 40% sodium hydroxide solution (7 cm$^3$) and a catalytic amount of tetra-n-butylammonium hydrogen sulphate (ca. 0.06 g) were mixed, then stirred vigorously at the ambient temperature (ca. 22° C.) for 36 hours. The mixture was poured into water, acidified using concentrated hydrochloric acid and extracted into diethyl ether. The combined ether extracts were washed twice with water, then dried over anhydrous magnesium sulphate. Evaporation of the solvent under reduced pressure gave an oil (0.82 g), from which the volatile components were removed by distillation in a Kugelrohr apparatus under reduced pressure (0.2 mmHg), at an oven temperature of 150° C. The residual oil was purified by chromatography on a silica gel support, eluting with n-hexane containing 5% by volume ethyl acetate, to give 1,1,1-trifluoro-2-(4-trifluoromethoxyphenyl)-3-(3-phenoxybenzyloxy))propan-2-ol as a colourless oil (0.2 g).

$^1$H NMR (CDCl$_3$) δ (ppm): ca. 3.7 (1H,dm); 3.74 (1H,s); ca. 4.08 (1H,d); 4.6 (2H,ABq); 6.9–7.6 (13H,m)

$^{19}$F NMR (CDCl$_3$) δ (relative to (CFCl$_3$): −58.3 (OCF$_3$); −77.7 (CF$_3$)

IR (liquid film): 3350 (OH), 1590, 1516, 1492, 1150–1290 cm$^{-1}$

GLC retention time: 9.92 minutes.

EXAMPLE 16

This Example illustrates the preparation of 1,1,1-trifluoro-2-(3-fluoro-4-ethoxyphenyl)-3-(3-phenoxybenzyloxy)propan-2-ol.

1,1,1-Trifluoro-2-(3-fluoro-4-ethoxyphenyl)propan-2,3-diol (0.4 g), prepared as described in Example 8 (ii), 3-phenoxybenzyl bromide (0.39 g), 40% sodium hydroxide solution (5cm$^3$), dichloromethane (5 cm$^3$) and tetra-n-butylammonium hydrogen sulphate (50 mg) were mixed, and stirred at room temperature under an atmosphere of nitrogen for 4½ hours. The reaction mixture was partitioned between water and dichloromethane. The organic layer was separated and the aqueous layer washed with dichloromethane. The combined organic layers were dried over anhydrous sodium sulphate and concentrated by evaporation under reduced pressure to give 1,1,1-trifluoro-2-(3-fluoro-4-ethoxyphenyl)-3-(3-phenoxybenzyloxy) propan-2-ol as an oil (0.67 g). The product was purified by column chromatography on a silica gel support, using n-hexane containing 15% by volume ethyl acetate as eluent.

$^1$H NMR (CDCl$_3$) δ (ppm): 1.44 (3H,t); 3.64 (1H,d); 3.65 (1H,s); 4.0–4.2 (1H,d and 2H,q); 4.57 (2H,ABq); 6.9–7.4 (12H,m).

GLC retention time: 11.61 minutes

EXAMPLE 17

This Example illustrates the Preparation of 1,1,1-trifluoro-2-(4-ethoxyphenyl)-3-bromopropan-2-ol.

A solution of 4-bromophenetole (20 g) in dry diethyl ether (25 cm$^3$) was added over 15 minutes to a mixture of magnesium (2.5 g) and dry diethyl ether (100 cm$^3$) containing iodine (0.1 g). The reaction was carried out under a nitrogen atmosphere. After gently warming the reaction vessel for a few minutes, the Grignard reaction began, and the addition rate was adjusted to maintain a gentle reflux. After all the 4-bromophenetole had been added the mixture was stirred for 1 hour at the ambient temperature (ca. 22° C.) and a solution of 1-bromo-3,3,3-trifluoropropan-2-one (19 g) in dry diethyl ether (20 cm$^3$) was then added dropwise over 40 minutes. The reaction mixture was then heated gently at the reflux temperature for 1 hour. After cooling, the reaction mixture was poured onto ice and acidified with hydrochloric acid. The layers were separated and the aqueous layer was extracted with diethyl ether (3×). The combined organic layers were washed with water, dried over anhydrous sodium sulphate and concentrated by evaporation of the solvent under reduced pressure. The residual oil was Purified by chromatography on a silica gel support to give the product as a pale brown oil (14 g).

$^1$H NMR (CDCl$_3$) δ (ppm): 1.44 (3H,t); 3.12 (1H,s); 3.9–4.2 (4H,m); ca. 6.9 (2H,m); 7.5 (2H,m).

GLC retention time: 7.39 minutes (50°–280° C. run).

EXAMPLE 18

This Example illustrates the preparation of 1,1,1-trifluoro-2-(4-ethoxyphenyl)-3-(6-phenoxy-2-pyridylmethyoxy)propan-2-ol.

1,1,1-Trifluoro-2-(4-ethoxyphenyl)-3-bromopropan-2-ol (1 g), prepared as described in Example 17, 6-phenoxy-2-pyridylmethanol (0.64 g), 40% sodium hydroxide solution (10 cm$^3$) and a catalytic amount of tetra-n-butylammonium hydrogen sulphate (ca. 0.1 g) were mixed at room temperature and stirred vigorously for 36 hours. The mixture was then poured into water and acidified with concentrated hydrochloric acid. The product was then extracted into diethyl ether. The combined ether extracts were washed with water, then dried over anhydrous magnesium sulphate. The solvent was removed by evaporation under reduced pressure to give an oil (1.2 g), from which volatile components were removed by distillation in a Kugelrohr apparatus under reduced pressure (0.2 mmHg), at an oven temperature of 150° C. The residual oil was purified by chromatography on a silica gel support; eluting with n-hexane containing 12.5% by volume ethyl acetate, to give 1,1,1-trifluoro-2-(4-ethoxyphenyl)-3-(6-phenoxy-2-pyridylmethoxy) propan-2-ol as a colourless oil (0.7 g).

$^1$H NMR (CDCl$_3$) δ (ppm): 1.4 (3H,t); 3.82 (1H,broadened d); 4.02 (2H,q); 4.12 (1H,d); 4.64 (2H,ABq); 4.83 (1H,s); 6.7–7.7 (12H,m).

$^{19}$F NMR (CDCl$_3$) δ (relative to (CFCl$_3$): −77.8

IR 3200–3600 cm$^{-1}$ (broad OH).

GLC retention time: 11.86 minutes.

EXAMPLE 19

By a procedure similar to that described in Example 18 above, the following compounds were prepared from the appropriate starting materials.

(i) 1,1,1-Trifluoro-2-(4-ethoxyphenyl)-3-(2-methyl-3-phenylbenzyloxy)propan-2-ol, from 1,1,1-trifluoro-2-(4-ethoxyphenyl)-3-bromopropan-2-ol and 2-methyl-3-phenylbenzyl alcohol.

$^1$H NMR (CDCl$_3$) δ (ppm): 1.4 (3H t ; 2.14 (3H,s); 3.7 (1H,s); 3.72 (1H,d); 4.04 (2H,q); 4.15 (1H,d); 4.64 (2H,ABq); 6.87 (2H,d); 7.2–7.5 (10H,m)

$^{19}$NMR (CDCl$_3$) δ (ppm - relative to (CFCl$_3$): −77.9 (CF$_3$,s)

GLC retention time: 12.01 minutes.

EXAMPLE 20

This Example illustrates the preparation of 1,1,1,2-tetrafluoro-2-(4-ethoxyphenyl)-3-(3-phenoxybenzyloxy) propane.

A solution of 1,1,1-trifluoro-2-(4-ethoxyphenyl)-3-(3-phenoxybenzyl)propan-2-ol (0.35 g) in dry dichloromethane (3 cm$^3$) was added to a solution of diethylaminosulphurtrifluoride (0.2 cm$^3$) in dry dichloromethane (4 cm$^3$), at a temperature of −78° C., under an atmosphere of nitrogen. The stirred mixture was allowed to warm to the ambient temperature (ca. 22° C.) over a period of 30 minutes, and was then stirred for a further 3 hours. After standing overnight, the reaction mixture was poured into water, and further dichloromethane, together with a saturated aqueous solution of sodium bicarbonate were added. The organic layer was separated, and the aqueous layer extracted twice with dichloromethane. The combined organic layers were dried over anhydrous sodium sulphate, and concentrated by evaporation under reduced pressure. Analysis of the residual oil by gas liquid chromatography and thin layer chromatography showed two principal components. These were separated by column chromatography on a silica gel support, using n-hexane containing 6% by volume ethyl acetate as eluent. The first component eluted (rf. 0.27 on silica gel plates eluted with n-hexane containing 5% ethyl acetate) was isolated as a colourless oil, and identified as the expected product, 1,1,1,2-tetrafluoro-2-(4-ethoxyphenyl)-3-(3-phenoxybenzyloxy)propane.

$^1$H NMR (CDCl$_3$) δ (ppm): 1.42 (3H,t); 4.0–4.1 (4H,m); 4.56 (2H,ABq); 6.9–7.4 (13H,m);

$^{19}$F NMR (CDCl$_3$) δ (ppm - relative to CFCl$_3$): −78.7 (CF$_3$,d); −175.4 (1F,m)

IR (liquid film): 1618, 1590, 1520, 1492, 1260, 1185 cm$^{-1}$

GLC retention time: 10.96 minutes.

The second component (rf. 0.21) was not isolated, but shown by mass spectrometry to be 1,1,1-trifluoro-2-(4-ethoxyphenyl)-3-(3-phenoxybenzyloxy) prop-2-ene, presumably resulting from de-hydrofluorination of the major product.

EXAMPLE 21

By use of a procedure similar to that described in Example 20 above, the following compounds were prepared from the appropriate starting materials.

(i) 1,1,1,2-Tetrafluoro-2-(4-ethoxyphenyl)-3-(6-phenoxy-2-pyridylmethyloxy)propane, from 1,1,1-trifluoro-2-(4-ethoxyphenyl)-3-(6-phenoxy-2-pyridylmethyloxy)propan-2-ol.

$^1$H NMR (CDCl$_3$) δ (ppm): 1.42 (3H,t); 4.05 (2H,q); ca. 4.16 (2H,d, Jhf=22 Hz); 4.6 (2H,s); 6.7–7.77 (12H,m)

$^{19}$F NMR (CDCl$_3$) δ (ppm - relative to (CFCl$_3$): −78.5 (3F,d); −100.3 (1F,m)

GLC retention time: 10.98 minutes.

(ii) 1,1,1,2-Tetrafluoro-2-(4-ethoxyphenyl)-3-(3-phenoxy-4-fluorobenzyloxy)propane, from 1,1,1-trifluoro-2-(4-ethoxyphenyl)-3-(3-phenoxy-4-fluorobenzyloxy)propan-2-ol.

$^1$H NMR (CDCl$_3$) δ (ppm): 1.42 (3H,t); 4.04 (4H,m); 4.52 (2H,ABq); 6.8–7.4 (12H,m)

$^{19}$F NMR (CDCl$_3$) δ (ppm - relative to (CFCl$_3$): −78.7 (3F,d); −132.4 (1F,m); −175.5 (1F,m)

IR (liquid film): 1617, 1593, 1515, 1493, 1430, 1290, 1260, 1180 cm$^{-1}$

GLC retention time: 10.88 minutes (iii) 1,1,1,2-Tetrafluoro-2-(4-ethoxyphenyl)-3-(4-methyl-2,3,5,6-tetrafluorobenzyloxy)propane, from 1,1,1-trifluoro-2-(4-ethoxyphenyl)-3-(4-methyl-2,3,5,6-tetrafluorobenzyloxy)propan-2-ol.

$^1$H NMR (CDCl$_3$) δ (ppm): 1.42 (3H,t); 2.27 (3H,t); 4.05 (2H,q); overlapping with 4.0 (1H,broad s); and 4.22 (1H, broad s); 4.68 (2H,m); ca. 6.9, 7.4 (4H,ABq)

$^{19}$F NMR (CDCl$_3$) δ (ppm - relative to (CFCl$_3$): −78.7 (3F,d); ca. −144.8 (4F,m) ca. −175.2 (1F,m)

IR (liquid film): 1617, 1520, 1492, 1290, 1260, 1180 cm$^{-1}$

GLC retention time: 7.27 minutes (iv) 1,1,1,2-tetrafluoro-2-(4-chlorophenyl) 3-(3-phenoxy-4-fluorobenzyloxy)propane from 1,1,1-trifluoro-2-(4-chlorophenyl)-3-(3-phenoxy-4-fluorobenzyloxy)propan-2-ol.

$^1$H NMR (CDCl$_3$) δ (ppm): 3.98 (1H,s); 4.07 (1H,ABq); 4.5 (2H,ABq); 6.85–7.4 (12H,m)

$^{19}$F NMR (CDCl$_3$) δ (ppm - relative to (CFCl$_3$): −78.6 (CF$_3$, d); −132.3 (1F,m); 176.3 (1F,m)

(v) 1,1,1,2-Tetrafluoro-2-(4-trifluoromethoxyphenyl)-3-(3-phenoxybenzyloxy)propane, from 1,1,1-trifluoro-2-(4-trifluoromathoxyphenyl)-3-(3-phenoxybenzyloxy)-propan-2-ol.

$^1$H NMR (CDCl$_3$) δ (ppm): 4.02 (1H,s); 4.1 (1H,ABq); 4.54 (2H,ABq); 6.8–7.5 (13H,m)

GLC retention time: 8.95 minutes (vi) 1,1,1,2-Tetrafluoro-2-(4-bromophenyl)-3-(3-phenoxy-4-fluorobenzyloxy)propane, from 1,1,1-trifluoro-2-(4-bromophenyl)-3-(3-phenoxy-4-fluorobenzyloxy)propan-2-ol.

$^1$H NMR (CDCl$_3$) δ (ppm): 3.98 (1H,s); 4.06 (1H,d); ca. 4.5 (2H, ABq); 6.9–7.6 (12H,m)

GLC retention time: 10.62 minutes (vii) 1,1,1,2-Tetrafluoro-2-(4-ethoxyphenyl)-3-(3-(4-chlorophenoxy)benzyloxy)propane, from 1,1,1-trifluoro-2-(4-ethoxyphenyl)-3-(3-(4-chlorophenoxy)benzyloxy)propan-2-ol.

$^1$H NMR (CDCl$_3$) δ (ppm): 1.4 (3H,t); 4.0–4.1 (4H,m); 4.56 (2H,ABq); 6.8–7.4 (12H,m)

$^{19}$F NMR (CDCl$_3$) δ (ppm - relative to (CFCl$_3$): −78.7 (CF$_3$,d); −175.5 (1F,m)

GLC retention time: 11.97 minutes (viii) 1,1,1,2-Tetrafluoro-2-(4-ethoxyphenyl)-3-(2-methyl-3-phenylbenzyloxy)propane, from 1,1,1-trifluoro-2-(4-ethoxyphenyl)-3-(2-methyl-3-phenylbenzyloxy)propan-2-ol.

$^1$H NMR (CDCl$_3$) δ (ppm): 1.42 (3H,t); 2.06 (3H,s); 4.04 (2H,q); ca. 4.12 (2H,d,J=23Hz); 4.66 (2H,ABq); 6.9 (2H,d); 7.2–7.5 (10H,m)

$^{19}$F NMR (CDCl$_3$) δ (ppm - relative to (CFCl$_3$): −78.7 (CF$_3$,d,J=7 Hz); −175.4 (1F,tq,J=7 Hz and 23 Hz)

GLC retention time: 11.17 minutes (ix) 1,1,1,2-Tetrafluoro-2-(4-trifluoromethylphenyl)-3-(3-phenoxybenzyloxy)propane.

$^1$H NMR (CDCl$_3$) δ (ppm): 4.0–4.2 (2H,m); 4.35 (2H,ABq); 6.8–7.7 (13H,m)

GLC retention time: 8.68 minutes

EXAMPLE 22

This Example illustrates the preparation of 1,1,1-trifluoro-2-acetoxy-2-(4-ethoxyphenyl)-3-(3-phenoxy-4-fluorobenzyloxy)propane.

1,1,1-Trifluoro-2-(4-ethoxyphenyl)-3-(3-phenoxy-4-fluorobenzyloxy)propan-2-ol (0.3 g), pyridine (1 cm$^3$), acetic anhydride (10 cm$^3$) and a catalytic amount of 4-N,N-dimethylaminopyridine (ca. 0.015 g) were mixed at the ambient temperature (ca. 22° C.), then heated at the reflux temperature for 6 hours. The mixture was allowed to stand overnight at the ambient temperature, and was then heated at reflux for a further 6 hours. Analysis by gas liquid chromatography showed 94% conversion to the product. Water was added and the product was extracted into diethyl ether (5×50 cm$^3$). The combined ether layers were dried over anhydrous sodium sulphate and concentrated by evaporation under reduced pressure. The residual oil was purified by column chromatography on a silica gel support, eluted with n-hexane containing 12% by volume ethyl acetate, to give 1,1,1-trifluoro-2-acetoxy-3-(3-phenoxy-4-fluorobenzyloxy)propane (0.29 g) as a viscous oil.

$^1$H NMR (CDCl$_3$) δ (ppm): 1.4 (3H,t); 2.13 (3H,s); 4.0 (2H,q); 4.39 (2H,broad s); 4.51 (2H, broad s); 6.8–7.5 (12H,m)

$^{19}$F NMR (CDCl$_3$) δ (ppm - relative to CFCl$_3$) −78.0 (3F,m); −132.9 (1F,m)

IR (liquid film) 1760, 1614, 1592, 1515, 1492, 1427, 1370, 1150–1300 cm$^{-1}$

GLC retention time: 12.22 minutes.

EXAMPLE 23

This Example illustrates the preparation of 1,1,1-trifluoro-2-methoxy-2-(4-ethoxyphenyl)-3-(3-phenoxy-4-fluorobenzyloxy)propane.

1,1,1-Trifluoro-2-(4-ethoxyphenyl)-3-(3-phenoxy-4-fluorobenzyloxy)propan-2-ol (0.2 g) in dry N,N-dimethyl-formamide (2 cm$^3$) was added to a suspension of sodium hydride (0.1 g of a 50% dispersion in oil - washed free of oil with n-hexane) in N,N-dimethylformamide (2 cm$^3$) at the ambient temperature (ca. 22° C.) under an atmosphere of nitrogen. After stirring for 20 minutes a solution of methyl iodide (0.1 g) in N,N-dimethylformamide (3 cm$^3$) was added in one portion. After 20 minutes no starting material could be detected by gas liquid chromatographic analysis. The mixture was carefully diluted with water (30 cm$^3$) then solid sodium chloride was added and the mixture shaken with diethyl ether. The layers were separated and the aqueous layer extracted with a further three portions of diethyl ether. The combined organic extracts were dried over anhydrous magnesium sulphate and the solvent removed by evaporation under reduced pressure. The resulting pale yellow oil was purified by chromatography on silica gel, eluting with n-hexane containing 10% by volume ethyl acetate to give 1,1,1-trifluoro-2-methoxy-2-(4-ethoxyphenyl)-3-(3-phenoxy-4-fluorobenzyloxy)propane as a colourless oil (0.2 g).

$^1$H NMR (CDCl$_3$) δ (ppm): 1.42 (3H,t); 3.34 (3H,s); 3.94 (2H,ABq) overlapping with 4.03 (2H,q); 4.52 (2H,s); 6.9–7.4 (12H,m)

$^{19}$F NMR (CDCl$_3$) δ (ppm - relative to (CFCl$_3$): −74.4 (CF$_3$,S); −132.7 (1F,m)

GLC retention time: 11.73 minutes

EXAMPLE 24

This Example illustrates the preparation of 1,1,1-trifluoro-2-chloro-2-(4-ethoxyphenyl)-3-(3-phenoxybenzyloxy) propane.

A solution of 1,1,1-trifluoro-2-(4-ethoxyphenyl)-3-(3-phenoxybenzyloxy)propan-2-ol (0.65 g) and imidazole (0.612 g) were dissolved in dry acetonitrile (30 cm$^3$), and the solution cooled to ca. 0° C. Thionyl chloride (1.21 g) was added dropwise, with stirring. The reaction mixture was allowed to warm to the ambient temperature (ca. 22° C.) and was stirred for a further three hours. Analysis of the reaction mixture by thin layer chromatography and gas liquid chromatography at that time showed no starting tertiary alcohol to be present. The reaction mixture was quenched with water, and a small volume of saturated sodium chloride solution was added. The aqueous mixture was extracted four times with diethyl ether and, finally, once with ethyl acetate. The combined organic layers were dried over anhydrous sodium sulphate and concentrated by evaporation of the solvent under reduced pressure to give an oil. The product was purified by column chromatography on a silica gel support, using n-hexane containing 6% by volume ethyl acetate as eluent, to give 1,1,1-trifluoro-2-chloro-2-(4-ethoxyphenyl)-3-(3-phenoxybenzyloxy)-propane (0.48 g) as a colourless oil.

$^1$H NMR (CDCl$_3$) δ (ppm): 1.41 (3H,t); 4.03 (2H,q); 4.06, 4.22 (2H,ABq); 4.62 (2H,ABq); 6.8–7.55 (13H,m)

$^{19}$F NMR (CDCl$_3$) δ (ppm - relative to (CFCl$_3$): −73.7 (CF$_3$)

IR (liquid film): 1617, 1590, 1518, 1492, 126 , 1220, 1185 cm$^{-1}$

GLC retention time: 11.90 minutes.

EXAMPLE 25

By use of a procedure similar to that described in Example 24 above, the following compounds were prepared from the appropriate starting materials.

(i) 1,1,1-Trifluoro-2-chloro-2-(4-ethoxyphenyl)-3-(4-methyl-2,3,5,6-tetrafluorobenzyloxy)propane, from 1,1,1-trifluoro-2-(4-ethoxyphenyl)-3-(4-methyl-2,3,5,6-tetrafluorobenzyloxy)propan-2-ol.

$^1$H NMR (CDCl$_3$) δ (ppm): 1.41 (3H,t); 2.28 (3H,t); 4.04 (2H,q) overlapping with 4.2 (2H,q); 4.73 (2H,m); ca. 6.9, 7.6 (4H,ABq)

$^{19}$F NMR (CDCl$_3$) δ (ppm - relative to CFCl$_3$): −73.7 (CF$_3$); ca. −144.7 (4F,m)

IR (liquid film): 1615, 1517, 1492, 1290, 1260, 1185 cm$^{-1}$

GLC retention time: 8.32 minutes.

(ii) 1,1,1-Trifluoro-2-chloro-2-(4-ethoxyphenyl)-3-(3-phenoxy-4-fluorobenzyloxy)propane, from 1,1,1-trifluoro-2-(4-ethoxyphenyl)-3-(3-phenoxy-4-fluorobenzyloxy)propan-2-ol.

$^1$H NMR (CDCl$_3$) δ (ppm): 1.42 (3H,t); 4.02 (2H,q); overlapping with 4.02 (1H,d); 4.2 (1H,d); 4.57 (1H,ABq); 6.8–7.6 (12H,m).

$^{19}$F NMR (CDCl$_3$) δ (ppm - relative to CFCl$_3$): −73.66 (CF$_3$); −132.4 (1F,m)

(iii) 1,1,1-Trifluoro-2-chloro-2-(4-ethoxyphenyl)-3-(6-phenoxy-2-pyridylmethyloxy)propane, from 1,1,1-trifluoro-2-chloro-2-(4-ethoxyphenyl)-3-(6-phenoxy-2-pyridylmethyloxy)propan-2-ol.

$^1$H NMR (CDCl$_3$) δ (ppm): 1.42 (3H,t); 4.05 (2H,q); 4.2, 4.35 (2H,ABq); 4.64 (2H,s); 6.7–7.7 (12H,m)

$^{19}$F NMR (CDCl$_3$) δ (ppm - relative to (CFCl$_3$): −73.6 (CF$_3$,S)

GLC retention time: 11.92 minutes.

(iv) 1,1,1-Trifluoro-2-chloro-2-(3-fluoro-4-ethoxyphenyl)-3-(3-(4-chlorophenoxy)benzyloxy) propane, from 1,1,1-trifluoro-2-(3-fluoro-4-ethoxyphenyl)-3-(3-(4-chlorophenoxy)benzyloxy)propan-2-ol.

$^1$H NMR (CDCl$_3$) δ (ppm): 1.45 (3H,t); 4.0–4.22 (4H,m); 4.62 (2H,ABq); 6 9–7.5 (11H,m)

GLC retention time: 12.70 minutes (NB. some decomposition on column to an olefin of retention time 11.99 minutes).

(v) 1,1,1-Trifluoro-2-chloro-2-(3-fluoro-4-ethoxyphenyl)-3-(3-phenoxybenzyloxy)propane, from 1,1,1-trifluoro-2-(3-fluoro-4-ethoxyphenyl)-3-(3-phenoxybenzyloxy)propan-2-ol.

$^1$H NMR (CDCl$_3$) δ (ppm): 1.45 (3H,t); 4.02 (1H,d); 4.11 (2H,q); 4.2 (1H,d); 4.62 (2H,ABq); 6.9–7.45 (12H,m)

$^{19}$F NMR (CDCl$_3$) δ (ppm - relative to (CFCl$_3$): −73.7 (CF$_3$,s); −134 (1F,m)

GLC retention time: 11.69 minutes (vi) 1,1,1-Trifluoro-2-chloro-2-(4-chlorophenyl)-3-(3-phenoxy-4-fluorobenzyloxy)propane (A) and 1,1,1-trifluoro-2-(4-chlorophenyl)-3-(3-phenoxy-4-fluorobenzyloxy)prop-2-ene (B), from 1,1,1-trifluoro-2-(4-chlorophenyl)-3-(3-phenoxy-4-fluorobenzyloxy)propan-2-ol.

The two products obtained in this case were separated by high pressure liquid chromatography on a silica gel support, using n-hexane containing 1% by volume ethyl acetate as eluent.

Product A: $^1$H NMR (CDCl$_3$) δ (ppm): ca. 4.0, 4.2 (2H,ABq); 4.55 (2H,s); 6.9–7.6 (12H,m)

$^{19}$F NMR (CDCl$_3$) δ (ppm - relative to (CFCl$_3$): −73.6 (CF$_3$,s); −132.4 (1F,m)

GLC retention time: 11.07 minutes.

Product B:
$^1$H NMR (CDCl$_3$) δ (ppm): 4.89 (2H,s); 6.9–7.5 (13H,m)

$^{19}$F NMR (CDCl$_3$) δ (ppm - relative to (CFCl$_3$): −61.9 (CF$_3$,s); −131.5 (1F,m)

GLC retention time: 10.42 minutes.

(vii) 1,1,1-Trifluoro-2-chloro-2-(4-fluorophenyl)-3-(3-phenoxy-4-fluorobenzyloxy) propane, from 1,1,1-trifluoro-2-(4-fluorophenyl)-3-(3-phenoxy-4-fluorobenzyloxy)propan-2-ol.

A small amount of enol ether (analogous to that isolated in (vi) above) was detected in the reaction mixture, but not isolated. Purification of the principal product was achieved by column chromatography on a silica gel support, using n-hexane containing 10% by volume ethyl acetate as eluent.

$^1$H NMR (CDCl$_3$) δ (ppm): 4.02, 4.20 (2H,ABq); 4.55 (2H,ABq); 6.9–7.6 (12H,m)

$^{19}$F NMR (CDCl$_3$) δ (ppm - relative to (CFCl$_3$): −73.7 (CF$_3$,s); −112.5 (1F,m); −132.4 (1F,m)

GLC retention time: 10.08 minutes.

(viii) 1,1,1,-Trifluoro-2 chloro-2-(5-indanyl)-3-(3-phenoxy-4-fluorobenzyloxy) propane (A) and 1,1,1-trifluoro-2-(5-indanyl)-3-(3-phenoxy-4-fluorobenzyloxy)-prop-2-ene (B) from 1,1,1-trifluoro-2-(5-indanyl)-3-(3-phenoxy-4-fluorobenzyloxy)propan-2-ol.

Products A and B were separated by preparative high pressure liquid chromatography on a silica gel support, using n-hexane containing 1% by volume ethyl acetate as eluent.

Product A:
$^1$H NMR (CDCl$_3$) δ (ppm): 2.09 (2H,m); 2.90 (4H,m); 4.05, 4.22 (2H,ABq); 4.56 (2H,ABq); 6.95–7.5 (11H,m)

$^{19}$F NMR (CDCl$_3$) δ (ppm - relative to CFCl$_3$): −73.3 (CF$_3$,s); −132.4 (1F,m)

GLC retention time: 12.18 minutes

Product B:
$^1$H NMR (CDCl$_3$) δ (ppm): 2.08 (2H,m); 2.90 (4H,m); 4.88 (2H,s); 6.9–7.4 (12H,m)

$^{19}$F NMR (CDCl$_3$) δ (ppm - relative to (CFCl$_3$): −62.2 (CF$_3$,s); −131.7 (1F,m).

GLC retention time: 11.42 minutes (ix) 1,1,1-Trifluoro-2-chloro-2-(4-n-propylphenyl)-3-(3-phenoxy-4-fluorobenzyloxy)propane (A) and 1,1,1-trifluoro-2-(4-n-propylphenyl)-3-(3-phenoxy-4-fluorobenzyloxy)prop-2-ene (B), from 1,1,1-trifluoro-2-(4-n-propylphenyl)-3-(3-phenoxy-4-fluorobenzyloxy)-propan-2-ol.

Products A and B were separated as described in (viii) above.

Product A:
$^1$H NMR (CDCl$_3$) δ (ppm): 0.96 (3H,t); 1.64 (2H,m); 2.61 (2H,t); 4.05, 4.20 (2H,ABq); 4.56 (2H,ABq); 6.9–7.5 (12H,m).

$^{19}$F NMR (CDCl$_3$) δ (ppm - relative to CFCl$_3$): −73.4 (CF$_3$,s); −132.5 (1F,m)

GLC retention time: 11.64 minutes.

Product B:
$^1$H NMR (CDCl$_3$) δ (ppm): 0.95 (3H,t); 1.64 (2H,m); 2.58 (2H,m); 4.9 (2H,s); 6.9–7.4 (13H,m)

$^{19}$F NMR (CDCl$_3$) δ (ppm - relative to CFCl$_3$): −62.0 (CF$_3$,s); −131.7 (1F,m).

GLC retention time: 10.95 minutes.

(x) 1,1,1-Trifluoro-2-chloro-2-(4-t-butylphenyl)-3-(3-phenoxy-4-fluorobenzyloxy)propane (A) and 1,1,1-trifluoro-2-(4-t-butylphenyl)-3-(3-phenoxy-4-fluorobenzyloxy)prop-2-ene (B), from 1,1,1-trifluoro-2-(4-t-butylphenyl)-3-(3-phenoxy-4-trifluorobenzyloxy)propan-2-ol.

Products A and B were separated as described in (viii) above.

Product A:
$^1$H NMR (CDCl$_3$) δ (ppm): 1.28 (9H,s); 4.05, 4.2 (2H,ABq); 4.55 (2H,ABq); 6.9–7.6 (12H,m)

$^{19}$F NMR (CDCl$_3$) δ (ppm - relative to CFCl$_3$): −73.3 (CF$_3$,s); −132.4 (1F,m)

GLC retention time: 11.78 minutes.

Product B:
$^1$H NMR (CDCl$_3$) δ (ppm): 1.28 (9H,s); 4.9 (2H,s); 6.9–7.4 (1H,m)

GLC retention time: 11.02 minutes.

(xi) 1,1,1-Trifluoro-2-chloro-2-(4-methylphenyl)-3-3-phenoxybenzyloxy)propane, from 1,1,1-trifluoro-2-(4-methylphenyl)-3-(3-phenoxybenzyloxy)propan-2-ol.

A small amount of enol ether (analogous to that isolated in (vi) above) was detected in the reaction mixture, but not isolated. The principal Product was purified as described in (vii) above.

$^1$H NMR (CDCl$_3$) δ (ppm): 2.35 (3H,s); ca. 4.16 (2H,ABq); 4.6 (2H,ABq); 6.9–7.6 (13H,m)

GLC retention time: 10.81 minutes.

(GLC retention time for the enol ether: 10.00 minutes).

(xii) 1,1,1-Trifluoro-2-chloro-2-(4-methoxymethylphenyl)-3-(3-(4-chlorophenoxy)benzyloxy)propane, from 1,1,1-trifluoro-2-(4-methoxymethylphenyl)-3-(3-(4-chloro-phenoxy)benzyloxy)propan-2-ol.

¹H NMR (CDCl₃) δ (ppm): 3.40 (3H,s); 4.08, 4.26 (2H,ABq); 4.48 (2H,s); 4.62 (2H,ABq); 6.9–7.7 (12H,m)
GLC retention time: 12.74 minutes.

(xiii) 1,1,1-Trifluoro-2-chloro-(4-methoxymethylphenyl)-3-(3-phenoxybenzyloxy)propane, from 1,1,1-trifluoro-2-(4-methoxymethylphenyl)-3-(3-phenoxybenzyloxy)propan-2-ol.

¹H NMR (CDCl₃) δ (ppm): 3.39 (3H,s); 4.06, 4.24 (2H,ABq); 4.46 (2H,s); 4.61 (2H,ABq); 6.9–7.7 (13H,m)
GLC retention time: 11.75 minutes.

(xiv) 1,1,1-Trifluoro-2-chloro-2-(4-trifluoromethoxyphenyl)-3-(3-phenoxy-4-fluorobenzyloxy)propane (A) and 1,1,1-trifluoro-2-(4-trifluoromethoxyphenyl)-3-(3-phenoxy-4-fluorobenzyloxy)prop-2-ene (B) from 1,1,1-trifluoro-2-(4-trifluoromethoxyphenyl)-3-(3-phenoxy-2-fluorobenzyloxy)Propan-2-ol.

Products A and B were separated as described in (viii) above.

Product A:
¹H NMR (CDCl₃) δ (ppm): 4.03, 4.24 (2H,ABq); 4.56 (2H,ABq); 6.95–7.7 (12H,m)
¹⁹F NMR (CDCl₃) δ (ppm - relative to CFCl₃):
−58.3 (CF₃O,s); −73.5 (CF₃,s); −132.9 (F,broad)
GLC retention time: 9.72 minutes Product B:
¹H NMR (CDCl₃) δ (ppm): 4.9 (2H,s); 6.9–7.4 (13H,m)
¹⁹F NMR (CDCl₃) δ (ppm - relative to CFCl₃):
−58.3 (CF₃O,s); −62.00 (CF₃,s); −132.0 (F,broad)
GLC retention time: 9.13 minutes.

(xv) 1,1,1-Trifluoro-2-chloro-2-(4-trifluoromethoxyphenyl)-3-(3-phenoxybenzyloxy)propane (A) and 1,1,1-trifluoro-2-(4-trifluoromethoxyphenyl)-3-(3-phenoxybenzyloxy)prop-2-ene (B) from 1,1,1-trifluoro-2-(4-trifluoromethoxyphenyl)-3-(3-phenoxybenzyloxy)propan-2-ol.

Products A and B were separated as described in (viii) above.

Product A:
¹H NMR (CDCl₃) δ (ppm): 4.03, 4.24 (2H,ABq); 4.61 (2H,ABq); 6.9–7.7 (11H,m); 7.66 (2H,d)
¹⁹F NMR (CDCl₃) δ (ppm - relative to CFCl₃):
−58.3 (CF₃O,s); −73.6 (CF₃,s)
GLC retention time: 9.88 minutes.

Product B:
¹H NMR (CDCl₃) δ (ppm): 4.96 (2H,s); 6.9–7.5 (14H,m)
¹⁹F NMR (CDCl₃) δ (ppm - relative to CFCl₃):
−58.3 (CF₃,s); −61.9 (CF₃,s)
GLC retention time: 9.26 minutes (xvi) 1,1,1-Trifluoro-2-chloro-2-(4-trifluoromethoxyphenyl)-3-(3-(4-chlorophenoxy)benzyloxy) propane (A) and 1,1,1-trifluoro-2-(4-trifluoromethoxyphenyl)-3-(3-(4-chlorophenoxy)benzyloxy)prop-2-ene (B) from 1,1,1-trifluoro-2-(4-trifluoromethoxyphenyl)-3-(3-(4-chlorophenoxy)benzyloxy)propan-2-ol.

Products A and B were separated as described in (viii) above.

Product A:
¹H NMR (CDCl₃) δ (ppm): 4.06, 4.26 (2H,ABq); 4.6 (2H,ABq); 6.9–7.7 (12H,m)
¹⁹F NMR (CDCl₃) δ (ppm - relative to CFCl₃):
−58.3 (CF₃O,s); −73.5 (CF₃,s)
GLC retention time: 10.81 minutes.

Product B:
¹H NMR (CDCl₃) δ (ppm): 4.96 (2H,s); 6.9–7.5 (14H,m)
¹⁹F NMR (CDCl₃) δ (ppm - relative to (CFCl₃):
−58.3 (CF₃O,s); −61.9 (CF₃,s); −66.0 (weak signal due to E isomer?)

(xvii) 1,1,1-Trifluoro-2-chloro-2-(4-methoxyphenyl)-3-(3-phenoxy-4-fluorobenzyloxy)propane, from 1,1,1-trifluoro-2-(4-methoxyphenyl)-3-(3-phenoxy-4-fluorobenzyloxy)propan-2-ol.

¹H NMR (CDCl₃) δ (ppm): 3.82 (3H,s); 4.05, 4.20 (2H,ABq); 4.56 (2H,ABq); 6.8–7.6 (12H,m)
¹⁹F NMR (CDCl₃) δ (ppm - relative to (CFCl₃):
−73.6 (3F,s); −132.5 (1F,m)
GLC retention time: not determinable - compound decomposed on the column.

(xviii) 1,1,1-Trifluoro-2-chloro-2-(4-methoxyphenyl)-3-(3-phenoxybenzyloxy)propane, from 1,1,1-trifluoro-2-(4-methoxyphenyl)-3-(3-phenoxybenzyloxy)propan-2-ol.

¹H NMR (CDCl₃) δ (ppm): 3.82 (3H,s); 4.05, 4.22 (2H,ABq); 4.64 (2H,ABq); 6.8–7.6 (13H,m).
¹⁹F NMR (CDCl₃) δ (ppm - relative to (CFCl₃):
−73.7 (CF₃)
GLC retention time: Not determinable - compound decomposed on the column.

(xix) 1,1,1-Trifluoro-2-chloro-2-(3,4-methylenedioxyphenyl)-3-(3-phenoxybenzyloxy)propane, from 1,1,1-trifluoro-2-(3,4-methylenedioxyphenyl)-3-(3-phenoxybenzyloxy)propan-2-ol.

¹H NMR (CDCl₃) δ (ppm): 4.02, 4.2 (2H,ABq); 4.60 (2H,ABq); 5.98 (2H,s); 6.8–7.4 (12H,m)
¹⁹F NMR (CDCl₃) δ (ppm - relative to (CFCl₃):
−73.6 (CF₃)
GLC retention time: 12.07 minutes.

(xx) 1,1,1-Trifluoro-2-chloro-2-(4-ethoxyphenyl)-3-(3-(4-chlorophenoxy)benzyloxy)propane, from 1,1,1-trifluoro-2-(4-ethoxyphenyl)-3-(3-(4-chlorophenoxy)benzyloxy)propan-2-ol.

¹H NMR (CDCl₃) δ (ppm): 1.43 (3H,t); 4.0–4.1 (2H,q) overlapping with (1H,d); 4.22 (1H,d); 4.63 (2H,ABq); 6.8–7.6 (12H,m)
¹⁹F NMR (CDCl₃) δ (ppm - relative to (CFCl₃):
−73.6 (CF₃,s)
GLC retention time: 12.93 minutes (xxi) 1,1,1-Trifluoro-2-chloro-2-(4-ethoxyphenyl)-3-(3-(4-bromophenoxy)-4-fluorobenzyloxy) propane, from 1,1,1-trifluoro-2-(4-ethoxyphenyl)-3-(3-(4-bromophenoxy)-4-fluorobenzyloxy)propan-2-ol.

¹H NMR (CDCl₃) δ (ppm): 1.42 (3H,t); 4.02 (2H,q); overlapping with 4.04 (1H,d); 4.20 (1H,d); 4.56 (2H,ABq); 6.8–7.5 (11H,m)
¹⁹F NMR (CDCl₃) δ (ppm - relative to CFCl₃):
−73.6 (3F,s); −131.1 (1F,m)
GLC retention time: 13.43 minutes (xxii) 1,1,1-Trifluoro-2-chloro-2-(4-ethoxyphenyl)-3-(3-(4-chlorophenoxy)-4-fluorobenzyloxy) propane, from 1,1,1-trifluoro-2-(4-ethoxyphenyl)-3-(3-(4-chlorophenoxy)-4-fluorobenzyloxy)propan-2-ol.

¹H NMR (CDCl₃)δ (ppm): 1.42 (3H,t); 4.02 (2H,q); overlapping with 4.34 (1H,d); 4.22 (1H,d); 4.56 (2H,s); 6.8–7.6 (11H,m)
¹⁹F NMR (CDCl₃) δ (ppm - relative to CFCl₃):
−73.6 (CF₃,s); −132.1 (1F,m)
GLC retention time: 12.67 minutes.

(xxiii) 1,1,1-Trifluoro-2-chloro-2-(4-ethoxyphenyl)-3-(5-benzyl-3-furanylmethyloxy)propane, from 1,1,1-trifluoro-2-(4-ethoxyphenyl)-3-(5-benzyl-3-furanylmethyloxy)propan-2-ol.

$^1$H NMR (CDCl$_3$) δ (ppm): 1.41 (3H,t); 3.95 (2H,s); ca. 4.05 (2H,q); overlapping with (1H,d); 4.20 (1H,d); 4.45 (2H,ABq); 6.0 (1H,s); 6.86 (2H,m); ca. 7.25 (6H,m); 7.56 (2H,m)

$^{19}$F NMR (CDCl$_3$) δ (ppm -relative to CFCl$_3$): −73.8 (CF$_3$,s)

(xxiv) 1,1,1-Trifluoro-2-chloro-2-(4-ethoxyphenyl)-3-(2-methyl-3-phenylbenzyloxy)propane, from 1,1,1-trifluoro-2-(4-ethoxyphenyl)-3-(2-methyl-3-phenylbenzyloxy)propan-2-ol.

$^1$H NMR (CDCl$_3$) δ (ppm): 1.42 (3H,t); 2.15 (3H,s); 4.04 (2H,q); 4.14, 4.3 (2H,ABq); 4.7 (2H,ABq); 6.87 (2H,d); 7.2–7.6 (10H,m)

$^{19}$F NMR (CDCl$_3$) δ (ppm - relative to CFCl$_3$): −73.7 (CF$_3$,s)

GLC retention time: 12.08 minutes (xxv) 1,1,1-Trifluoro-2-chloro-2-(3,4-methylenedioxyphenyl)-3-(3-(4-chlorophenoxy)-benzyloxy) propane, from 1,1,1-trifluoro-2-(3,4-methylenedioxyphenyl)-3-(3-(4-chlorophenoxy)benzyloxy)propan-2-ol.

$^1$H NMR (CDCl$_3$) δ (ppm): 4.04, 4.20 (2H,d); 4.61 (2H,ABq); 5.98 (2H,s); 6.77 (1H,d); 6.9–7.4 (10H,m)

$^{19}$F NMR (CDCl$_3$) δ (ppm - relative to CFCl$_3$): −73.6 (CF$_3$,s)

GLC retention time: 13.07 minutes (xxvi) 1,1,1-Trifluoro-2-chloro-2-(4-trifluoromethoxy-3-(6-phenoxy-2-pyridylmethyloxy)propane from 1,1,1-trifluoro-2-(4-trifluoromethoxy)-3-(6-phenoxy-2-pyridylmethyloxy)propan-2-ol.

$^1$H NMR (CDCl$_3$) δ (ppm): 4.16 (1H,d); 4.36 (1H,d); 4.61 (2H,s); 6.7–7.8 (12H,m)

$^{19}$F NMR (CDCl$_3$) δ (ppm - relative to CFCl$_3$): −58.3 CF$_3$O,s); −73.5 (CF$_3$,s)

GLC retention time: 9.60 minutes.

(xxvii) 1,1,1-Trifluoro-2-chloro-2-(4-ethoxyphenyl)-3-(3-benzyl-4-fluorobenzyloxy)propane, from 1,1,1-trifluoro-2-(4-ethoxyphenyl)-3-(3-benzyl-4-fluorobenzyloxy)propan-2-ol.

$^1$H NMR (CDCl$_3$) δ (ppm): 1.4 (3H,t); 3.9–4.2 (6H,m); 4.6 (2H,q); 6.8–7.6 (12H,m)

$^{19}$F NMR (CDCl$_3$) δ (ppm - relative to CFCl$_3$): −73.6 (3F); −119.5 (1F)

EXAMPLE 26

This Example illustrates the preparation of 1,1,1-trifluoro-2-(4-ethoxyphenyl)-3-(3-phenoxybenzyloxy)propane.

A few crystals of α,α-azoisobutyronitrile (AIBN) were added to a solution of 1,1,1-trifluoro-2-chloro-2-(4-ethoxyphenyl)-3-(3-phenoxybenzyloxy)propane (0.36 g) in toluene (15 cm$^3$), and the mixture was cooled in an ice bath whilst tri-n-butyl tin hydride (0.25 cm$^3$) was added. The reaction mixture was heated at the reflux temperature for 1.5 hours under an atmosphere of nitrogen. Analysis by gas liquid chromatography at this time showed no trace of the starting chloro compound. The mixture was cooled, poured I into water (50 cm$^3$), and extracted with diethyl ether (4×30 cm$^3$). The combined organic layers were dried over anhydrous sodium sulphate and the residual oil after evaporation of the solvent under reduced pressure was purified by column chromatography on a silica gel support, eluting with n-hexane containing 6% by volume diethyl ether, to give 1,1,1-trifluoro-2-(4-ethoxyphenyl)-3-(3-phenoxybenzyloxy)-propane (0.3 g) as an oil.

$^1$H NMR (CDCl$_3$) δ (ppm): 1.42 (3H,t); 3.55 (1H,q); 3.8 (1H,m); 3.95 (1H,m); 4.0 (2H,q); 4.46 (ABq,2H); 6.8–7.4 (13H,m)

IR (liquid film): 1617, 1590, 1520, 1490, 1260, 1220, 1170, 1126, 700 cm$^{-1}$

GLC retention time: 11.15 minutes.

EXAMPLE 27

By use of a procedure similar to that described in Example 26 above, the following compounds were prepared from the appropriate starting materials:

(i) 1,1,1-Trifluoro-2-(4-ethoxyphenyl)-3-(4-methyl-2,3,5,6-tetrafluorobenzyloxy)propane, from 1,1,1-trifluoro-2-chloro-2-(4-ethoxyphenyl)-3-(4-methyl-2,3,5,6-tetrafluorobenzyloxy)propane. The product was obtained in the form of a white crystalline solid of melting point 77°–78° C.

$^1$H NMR (CDCl$_3$) δ (ppm): 1.4 (3H,t); 2.26 (3H,t); ca. 3.52 (1H,m); 3.8 (1H,m); 4.02 (2H,q) overlapping with ca. 4.0 (1H,m); 4.58 (2H,s); ca. 6.85, 7.2 (4H,ABq)

IR: 1615, 1516, 1490, 1290, 1260, 1186 cm$^{-1}$

GLC retention time: 7.30 minutes.

(ii) 1,1,1-Trifluoro-2-(3-fluoro-4-ethoxyphenyl)-3-(3-(4-chlorophenoxy)benzyloxy)propane, from 1,1,1-trifluoro-2-chloro-2-(3-fluoro-4-ethoxyphenyl)-3-(3-(4-chlorophenoxy)benzyloxy) propane.

$^1$H NMR (CDCl$_3$) δ (ppm): 1.44 (3H,t); 3.52 (1H,m); 3.77 (1H,t); 3.92 (1H,dd); 4.1 (2H,q); 4.45 (2H,ABq); 6.8–7.3 (11H,m)

GLC retention time: 11.90 minutes.

(iii) 1,1,1-Trifluoro-2-(3-fluoro-4-ethoxyphenyl)-3-(3-phenoxybenzyloxy)propane, from 1,1,1-trifluoro-2-chloro-2-(3-fluoro-4-ethoxyphenyl)-3-(3-phenoxybenzyloxy)propane.

$^1$H NMR (CDCl$_3$) δ (ppm): 1.44 (3H,t); 3.5 (1H,m); 3.76 (1H,dd); 3.9 (1H,dd); 4.08 (2H,q); 4.46 (2H,ABq); 6.8–7.4 (12H,m)

$^{19}$F NMR (CDCl$_3$) (ppm - relative to CFCl$_3$): −68.5 (3F,d); −134.1 (1F,m)

GLC retention time: 10.91 minutes.

(iv) 1,1,1-Trifluoro-2-(4-chlorophenyl)-3-(3-phenoxy-4-fluorobenzyl)propane, from 1,1,1-trifluoro-2-chloro-2-(4-chlorophenyl)-3-(3-phenoxy-4-fluorobenzyloxy)propane.

$^1$H NMR (CDCl$_3$) δ (ppm): 3.55 (1H,m); 3.76 (1H,t); 3.9 (1H,dd); 4.2 (2H,ABq); 6.8–7.4 (12H,m)

$^{19}$F NMR (CDCl$_3$) δ (ppm - relative to CFCl$_3$): −68.2 (CF$_3$,d); −132.6 (1F,m)

GLC retention time: 10.45 minutes (v) 1,1,1-Trifluoro-2-(4-fluorophenyl)-3-(3-phenoxy-4-fluorobenzyloxy)propane, from 1,1,1-trifluoro-2-chloro-2-(4-fluorobenzyl)-3-(3-phenoxy)-4-fluorobenzyloxy)propane.

$^1$H NMR (CDCl$_3$) δ (ppm): 3.58 (1H,m); 3.78 (1H,t); 3.9 (1H,dd); 4.40 (2H,ABq); 6.8–7.4 (12H,m)

$^{19}$F NMR (CDCl$_3$) δ (ppm - relative to CFCl$_3$): −68.4 (CF$_3$,d); −114.1 (1F,m); −132.7 (1F,m)

GLC retention time: 9.31 minutes.

(vi) 1,1,1-Trifluoro-2-(5-indanyl)-3-(3-phenoxy-4-fluorobenzyloxy)propane, from 1,1,1-trifluoro-2-chloro-2-(5-indanyl)-3-(3-phenoxy-4-fluorobenzyloxy)propane.

$^1$H NMR (CDCl$_3$) δ (ppm): 2.07 (2H,m); 2.86 (4H,m); 3.55 (1H,m); 3.78 (1H,t); 3.95 (1H,dd); 4.44 (2H,ABq); 6.9–7.4 (11H,m)

$^{19}$F NMR (CDCl$_3$) δ (ppm - relative to (CFCl$_3$): −68.1 (CF$_3$,d); −132.7 (1F,m)

GLC retention time: 11.37 minutes.

(vii) 1,1,1-Trifluoro-2-(4-n-propylphenyl)-3-(3-phenoxy-4-fluorobenzyloxy)propane, from 1,1,1-trifluoro-2-chloro-2-(4-n-propylphenyl)-3-(3-phenoxy-4-fluorobenzyloxy)propane.

¹H NMR (CDCl₃) δ (ppm): 0.95 (3H,t); 1.62 (2H,m); 2.58 (2H,t); 3.55 (1H,m); 3.8 (1H,t); 3.96 (1H,dd); 4.4 (2H,ABq); 6.9–7.4 (12H,m)

¹⁹F NMR (CDCl₃) δ (ppm - relative to CFCl₃): −68.1 (CF₃, d): −132.8 (1F,m)

GLC retention time: 10.84 minutes.

(viii) 1,1,1-Trifluoro-2-(4-t-butylphenyl)-3-(3-phenoxy-4-fluorobenzyloxy)propane, from 1,1,1-trifluoro-2-chloro-2-(4-t-butylphenyl)-3-(3-phenoxy-4-fluorobenzyloxy)propane.

¹H NMR (CDCl₃) δ (ppm): 1.24 (9H,s); 3.5 (1H,m); 3.71 (1H,dd); 3.9 (1H,dd); 4.36 (2H,ABq); 6.8–7.3 (12H,m)

¹⁹F NMR (CDCl₃) δ (ppm - relative to CFCl₃): −68.1 (CF₃,d); −132.7 (1F,m)

GLC retention time: 10.91 minutes (ix) 1,1,1-Trifluoro-2-(4-methylphenyl)-3-(3-phenoxybenzyloxy)propane, from 1,1,1-trifluoro-2-chloro-2-(4-methylphenyl)-3-(3-phenoxybenzyloxy)propane.

¹H NMR (CDCl₃) δ (ppm): 2.32 (3H,s): 3.58 (1H,m): 3.81 (1H,m); 3.97 (1H,m): 4.48 (2H,ABq); 6.9–7.4 (13H,m)

¹⁹F NMR (CDCl₃) δ (ppm - relative to CFCl₃)

GLC retention time: 9.85 minutes (x) 1,1,1-Trifluoro-2-(4-methoxymethylphenyl)-3-(3-(4-chlorophenyl)benzyloxy)propane, from 1,1,1-trifluoro-2-chloro-2-(4-methoxymethylphenyl)-3-(3-(4-chlorophenoxy)benzyloxy)propane.

¹H NMR (CDCl₃) δ (ppm): 3.39 (3H,s ; 3.64 (1H,m); 3.82 (1H,t); 4.0 (1H,dd); 4.43 (2H,s); overlapping with 4.45 (2H,ABq); 6.8–7.4 (12H,m)

GLC retention time: 12.10 minutes (xi) 1,1,1-Trifluoro-2-(4-methoxymethylphenyl)-3-(3-phenoxybenzyloxy)propane, from 1,1,1-trifluoro-2-chloro-2-(4-methoxymethylphenyl)-3-(3-phenoxybenzyloxy)propane.

¹H NMR (CDCl₃) δ (ppm): 3.38 (3H,s); 3.64 (1H,m); 3.82 (1H,t); 4.0 (1H,dd); 4.44 (2H,s); overlapping with 4.46 (2H,ABq); 6.9–7.4 (13H,m)

GLC retention time: 11.09 minutes (xii) 1,1,1-Trifluoro-2-(4-trifluoromethoxyphenyl)-3-(3-phenoxy-4-fluorobenzyloxy)propane, from 1,1,1-trifluoro-2-chloro-2-(4-trifluoromethoxyphenyl)-3-(3-phenoxy-4-fluorobenzyloxy)propane.

¹H NMR (CDCl₃) δ (ppm): 3.64 (1H,m); 3.8 (1H,t); 3.95 (1H,dd); 4.4 (2H,ABq); 6.9–7.4 (12H,m)

GLC retention time: 9.03 minutes (xiii) 1,1,1-Trifluoro-2-(4-trifluoromethoxyphenyl)-3-(3-(4-chlorophenoxy)benzyloxy)propane, from 1,1,1-trifluoro-2-chloro-2-(4-trifluoromethoxyphenyl)-3-(3-(4-chlorophenoxy)benzyloxy)propane.

¹H NMR (CDCl₃) δ (ppm): 3.65 (1H,m); 3.82 (1H,t); 3.98 (1H,dd); 4.5 (2H,ABq); 6.8–7.4 (12H,m)

GLC retention time: 10.17 minutes (xiv) 1,1,1-Trifluoro-2-(4-trifluoromethoxyphenyl)-3-(3-phenoxybenzyloxy)propane, from 1,1,1-trifluoro-2-chloro-2-(4-trifluoromethoxyphenyl)-3-(3-phenoxybenzyloxy)propane.

¹H NMR (CDCl₃) δ (ppm): 3.65 (1H,m); 3.82 (1H,t); 3.95 (1H,dd); 4.48 (2H,ABq); 6.9–7.4 (13H,m)

¹⁹F NMR (CDCl₃) δ (ppm - relative to CFCl₃): −58.3 (CF₃O,s); −68.2 (CF₃,d)

GLC retention time: 9.24 minutes (xv) 1,1,1-Trifluoro-2-(4-methoxyphenyl)-3-(3-phenoxy-4-fluorobenzyloxy)propane, from 1,1,1-trifluorochloro-2-(4-methoxyphenyl)-3-(3-phenoxy-4-fluorobenzyloxy)propane.

¹H NMR (CDCl₃) δ (ppm): 3.56 (1H,m); 3.8 (3H,s); overlapping with (1H,m); 3.95 (1H,m); 4.42 (2H,ABq); 6.8–7.4 (12H,m)

¹⁹F NMR (CDCl₃) δ (ppm - relative to CFCl₃): −68.5 (CF₃,d); −132.7 (1F,m)

GLC retention time: 10.76 minutes (xvi) 1,1,1-Trifluoro-2-(4-methoxyphenyl)-3-(3-phenoxybenzyloxy)propane, from 1,1,1-trifluoro-2-chloro-2-(4-methoxyphenyl)-3-(3-phenoxybenzyloxy)propane.

¹H NMR (CDCl₃) δ (ppm): 3.58 (1H,m); 3.80 (3H,s) overlapping with (1H,m); 3.96 (1H,m); 4.48 (2H,ABq); 6.8–7.4 (13H,m)

GLC retention time : 10.84 minutes (xvii) 1,1,1-Trifluoro-2-(3,4-methylenedioxyphenyl)-3-(3-phenoxybenzyloxy)propane from 1,1,1-trifluoro-2-chloro-2-(3,4-methylenedioxyphenyl)-3-(3-phenoxybenzyloxy)propane.

¹H NMR (CDCl₃) δ (ppm): 3.52 (1H,m); 3.77 (1H,t); 3.95 (1H,dd); 4.48 (2H,Abq); 5.95 (2H,s); 6.7–7.4 (12H,m)

GLC retention time: 11.20 minutes (xviii) 1,1,1-Trifluoro-2-(3,4-methylenedioxyphenyl)-3-(3-(4-chlorophenoxy)benzyloxy)propane, from 1,1,1-trifluoro-2-chloro-2-(3,4-methylenedioxyphenyl)-3-(3-(4-chlorophenoxy)benzyloxy) propane.

¹H NMR (CDCl₃) δ (ppm): 3.55 (1H,m); 3.77 (1H,t); 3.94 (1H,dd); 4.48 (2H,ABq); 5.95 (2H,s); 6.75–7.4 (11H,m)

¹⁹F NMR (CDCl₃) δ (ppm - relative to CFCl₃): −68.4 (CF₃,d)

GLC retention time: 12.16 minutes (xix) 1,1,1-Trifluoro-2-(4-ethoxyphenyl)-3-(3-(4-chlorophenoxy)benzyloxy)propane, from 1,1,1-trifluoro-2-chloro-2-(4-ethoxyphenyl)-3-(3-(4-chlorophenoxy)benzyloxy)propane.

¹H NMR (CDCl₃) δ (ppm): 1.41 (3H,t); 3.56 (1H,m); 3.80 (1H,t); 3.9–4.1 (2H,q) overlapping with (1H,dd); 4.48 (2H,ABq); 6.8–7.4 (12H,m)

¹⁹F NMR (CDCl₃) δ (ppm - relative to CFCl₃): −68.4 (CF₃,d)

GLC retention time: 11.92 minutes.

(xx) 1,1,1-Trifluoro-2-(4-ethoxyphenyl)-3-(6-phenoxy-2-pyridylmethyloxy)propane, from 1,1,1-trifluoro-2-chloro-2-(4-ethoxyphenyl)-3-(6-phenoxy-2-pyridylmethyloxy)propane.

¹H NMR (CDCl₃) δ (ppm): 1.41 (3H,t); 3.6 (1H,m); 3.88 (1H,dd); ca. 4.02 (3H,m); 4.52 (2H,s); 6.7–7.7 (12H,m)

¹⁹F NMR (CDCl₃) δ (ppm - relative to CFCl₃): −68.3 (CF₃,d)

GLC retention time: 11.28 minutes.

(xxi) 1,1,1-Trifluoro-2-(4-ethoxyphenyl)-3-(3-(4-chlorophenoxy)4-fluorobenzyloxy)propane, from 1,1,1-trifluoro-2-chloro-2-(4-ethoxyphenyl)-3-(3-(4-chlorophenoxy)-4-fluorobenzyloxy)propane.

¹H NMR (CDCl₃) δ (ppm): 1.42 (3H,t); 3.56 (1H,m); 3.78 (1H,t); 3.95 (1H,dd) overlapping with 4.02 (2H,q); 4.4 (2H,ABq); 6.8–7.3 (11H,m)

¹⁹F NMR (CDCl₃) δ (ppm - relative to CFCl₃): −68.4 (CF₃,d); −132.4 (1F,m)

GLC retention time: 11.91 minutes.

(xxii) 1,1,1-Trifluoro-2-(4-ethoxyphenyl)-3-(3-(4-bromophenoxy)-4-fluorobenzyloxy)propane, from 1,1,1-trifluoro-2-chloro-2-(4-ethoxyphenyl)-3-(3-(4-bromophenoxy)-4-fluorobenzyloxy)propane.

¹H NMR (CDCl₃) δ (ppm): 1.40 (3H,t); ca. 3.55 (1H,m); 3.78 (1H,t); 3.94 (1H,dd) overlapping with 4.0 (2H,q); 4.4 (2H,ABq); 6.8–7.45 (11H,m)

¹⁹F NMR (CDCl₃) δ (ppm - relative to CFCl₃): −68.4 (3F,d); −132.3 (1F,m)

GLC retention time: 12.47 minutes (xxiii) 1,1,1-Trifluoro-2-(4-ethoxyphenyl)-3-(2-methyl-3-phenylbenzyloxy)propane, from 1,1,1-trifluoro-2-chloro-2-(4-ethoxyphenyl)-3-(2-methyl-3-phenylbenzyloxy)propane.

¹H NMR (CDCl₃) δ (ppm): 1.42 (3H,t); 2.06 (3H,s); 3.6 (1H,m); 3.88 (1H,t); 3.95–4.1 (2H,q) overlapping with (1H,m); 4.55 (2H,ABq); 6.86 (2H,d); 7.2–7.5 (10H,m)

¹⁹F NMR (CDCl₃) δ (ppm - relative to CFCl₃): −68.5 (CF₃,d)

GLC retention time: 11.39 minutes (xxiv) 1,1,1-Trifluoro-2-(4-trifluoromethoxyphenyl)-3-(6-phenoxy-2-pyridylmethyloxy)propane, from 1,1,1-trifluoro-2-chloro-(4-trifluoromethoxyphenyl)-3-(6-phenoxy-2-(pyridylmethyloxy)propane.

¹H NMR (CDCl₃) δ (ppm): 3.66 (1H,m); 3.9 (1H,dd); 4.06 (1H,dd); 4.48 (2H,ABq); 6.7–7.65 (12H,m)

GLC retention time: 8.89 minutes (xxv) 1,1,1,-Trifluuoro-2-(4-ethoxyphenyl)3-(3-benzyl-4-fluorobenzyloxy)propane, from 1,1,1-trifluoro-2-chloro-2-(4-ethoxyphenyl)-3-(3-benzyl-4-fluorobenzyloxy)propane.

¹H NMR (CDCl₃) δ (ppm): 1.4 (3H,t); 3.5 (1H,m); 3.75 (1H,dd); 4.0 (5H,m); 4.4 (2H,q); 6.8–7.3 (12H,m)

¹⁹F NMR (CDCl₃) δ (ppm - relative to CFCl₃): −68.45 (3F,d); −119.89 (1F,q)

GLC retention time: 9.98 minutes

EXAMPLE 28

This Example illustrates the steps in the preparation of 1,1,1-trifluoro-2-(4-ethoxyphenyl)propan-3-ol.

Stage 1: Preparation of 1,1,1,3,3-pentafluoro-2-(4-ethoxyphenylphenyl)-3-chloropropan-2-ol.

A mixture of ethoxybenzene (67 g), chloropentafluoroacetone (100 g) and aluminium chloride (7 g) was charged to a Hastalloy lined cell at −78° C., the cell sealed and heated to 120° C. for 8 hours. After cooling and venting, the residue was taken up in chloroform and filtered through silica gel. After removal of the solvent by evaporation the residual solid was recrystallised from n-hexane to yield several crops of 1,1,1,3,3-pentafluoro-2-(4-ethoxyphenyl)-3-chloropropan-2-ol. (Total 70 g) mp. 84°–86° C.

¹H NMR (CDCl₃) δ (ppm): 1.43 (t,3H); 3.44 (s,1H); 4.07 (q,2H); 6.95, 7.8 (m,2H)

¹⁹F NMR (CDCl₃) δ (ppm - relative to CFCl₃): −62.4 (q,2F); −76 (t,CF₃)

Stage 2: Preparation of 1,1,1,3,3-pentafluoro-2,3-dichloro-2-(4-ethoxyphenyl)propane A mixture of 1,1,1,3,3-pentafluoro-2-(4-ethoxyphenyl)-3-chloropropan-2-ol (28 g), thionyl chloride (45 cm³) and pyridine (3 cm³) was heated at the reflux temperature for 4 hours, diluted with toluene and the volatile components removed by evaporation under reduced pressure. The residual oil was dissolved in chloroform, washed with water and dried over anhydrous magnesium sulphate. Removal of the solvent by evaporation under reduced pressure yielded 1,1,1,3,3-pentafluoro-2,3-dichloro-2-(4-ethoxyphenyl)propane (29.5 g) as a residual oil.

IR (liquid film): 1616, 1516, 1305, 1180–1270, 1050, 924, 825, 736, 701 cm⁻¹

¹H NMR (CDCl₃) δ (ppm): 1.42 (t,3H); 4.06 (q,2H); 6.9, 7.72 (m,4H)

¹⁹F NMR (CDCl₃ δ (ppm - relative to CFCl₃): −68.42 (t,3F:J$_{FF}$J=12 Hz); −56.8 (dd,2F:J$_{FF}$J=12 Hz and 170 Hz)

Stage 3: Preparation of 1,1,1,3,3-pentafluoro-2,3-dichloro-2-(4-ethoxyphenyl)prop-2-ene.

A solution of 1,1,1,3,3-pentafluoro-2,3-dichloro-2-(4-ethoxyphenyl)propane (29.5 g) in methanol (40 cm³) was added dropwise to a suspension of zinc powder (9.1 g) and zinc chloride (0.45 g) in methanol (80 cm³) whilst the temperature was maintained at 35° C. After the addition was complete the mixture was stirred at the ambient temperature (ca. 23° C.) for 2 hours. After dilution with water and filtering off the zinc, the mixture was extracted with chloroform, the extracts washed with water, dried over anhydrous magnesium sulphate and concentrated by evaporation of the solvent to yield 1,1,1,3,3-pentafluoro-2-(4-ethoxyphenyl)prop-2-ene (19.0 g) as a mobile liquid.

IR (liquid film): 1735, 1617, 1520, 1360, 1295, 1250, 1180, 1130, 1075, 950 cm⁻¹

¹H NMR (CDCl₃) δ (ppm): 1.41 (t,3H); 4.05 (q,2H); 6.9, 7.25 (m,4H, AB System).

¹⁹F NMR (CDCl₃) δ (ppm - relative to CFCl₃): −60.1 (dd,3F, J=25 and 10.5 Hz); −76.86 (dq,1F, J=25 and 15 Hz); −78.60 (dt,1F, J=12.5 and 10.5 Hz)

Stage 4: Preparation of a mixture of 1,1,1,3,3-pentafluoro-2-(4-ethoxyphenyl)-3-ethoxypropane and (Z)- and (E)-isomers of 1,1,1,3-tetrafluoro-2-(4-ethoxyphenyl)-3-ethoxyprop-2-ene.

A solution of sodium ethoxide obtained by dissolving sodium (1.74 g) in ethanol (100 cm³) was added dropwise to a stirred solution of 1,1,1,3,3-pentafluoro-2-(4-ethoxyphenyl)prop-2-ene (19 g) in ethanol (100 cm³) at 10° C. after which the mixture was allowed to warm to the ambient temperature over a period of one hour. The mixture was quenched with water, acidified with concentrated hydrochloric acid (15 cm³), and extracted with chloroform. The extracts were washed with water twice, dried over anhydrous magnesium sulphate and concentrated by evaporation of the solvent under reduced pressure to yield a mobile oil (19.7 g). Gas liquid chromatographic and mass spectrographic analysis indicated this to be a mixture comprising 1,1,1,3,3-pentafluoro-2-(4-ethoxyphenyl)-3-ethoxypropane (16% by weight), (Z)-1,1,1,3-tetrafluoro-2-(4-ethoxyphenyl)-3-ethoxyprop-2-ene (61% by weight and (E)-1,1,1,3-tetrafluoro-2-(4-ethoxyphenyl)-3-ethoxyprop-2-ene (16% by weight). This was used without further purification in the next stage.

Stage 5: Preparation of 1,1,1-trifluoro-2-(4-ethoxyphenyl)propionic acid

The mixture obtained in the previous stage (19 g) was heated with glacial acetic acid (75 cm³) and hydriodic acid (58%, w/v, 18 g) at the reflux temperature for 24 hours. After cooling, the mixture was diluted with water and extracted with chloroform. The extracts were washed with water three times, dried over anhydrous magnesium sulphate and concentrated by evaporation of the solvent under reduced pressure to yield an oil (18.1 g) which was redissolved in chloroform and extracted with aqueous saturated sodium bicarbonate solution. The aqueous solution was acidified with hydrochloric acid and extracted with chloroform. The chloroform extracts were dried over anhydrous magnesium sulphate and concentrated by evaporation of the solvent under reduced pressure to yield 1,1,1-trifluoro-2-(4-ethoxyphenyl)propionic acid (7.5 g).

$^1$H NMR (CDCl$_3$) δ (ppm): 1.39 (t,3H); 3.95 (q,2H); 4.20 (q,1H); 6.8, 7.2 (m,4H); 8.65 (broad s, 1H)

The chloroform phase remaining after extraction with sodium bicarbonate was dried over anhydrous magnesium sulphate and concentrated by evaporation of the solvent under reduced pressure to yield ethyl 1,1,1-trifluoro-2-(4-ethoxyphenyl)propionate, purified by distillation in a kugelrohr apparatus at 0.2 mm (oven temperature 80°-100° C.).

Stage 6: Preparation of ethyl 1,1,1-trifluoro-2-(4-ethoxyphenyl)propionate

A mixture of 1,1,1-trifluoro-2-(4-ethoxyphenyl)propionic acid (6.5 g), ethanol (100 cm$^3$) and concentrated hydrochloric acid (2.0 cm$^3$) was heated at the reflux temperature for 5 hours after which the excess of ethanol was removal by evaporation under reduced pressure. The residue was partitioned between water and chloroform and the chloroform layer washed with water, dried over anhydrous magnesium sulphate and concentrated by evaporation of the solvent under reduced pressure to yield an oil (6.7 g) which was further purified by distillation in a kugelrohr apparatus at 0.2 mm (oven temperature 100°-120° C.) to yield ethyl 1,1,1-trifluoro-2-(4-ethoxyphenyl)propionate (5.6 g).

$^1$H NMR (CDCl$_3$) δ (ppm): 1.25 (t,3H); 1.41 (t,3H); 3.9-4.4 (m,5H); 6.9, 7.35 (m,4H)

$^{19}$F NMR (CDCl$_3$) δ (ppm - relative to CFCl$_3$): −68 53 (d,3F, $J_{HF}$=8.37 Hz).

Stage 7: Preparation of 1,1,1-trifluoro-2-(4-ethoxyphenyl)propan-3-ol

Diisobutylaluminium hydride (30 cm$^3$ of a 1M solution in n-hexane) was added dropwise to a stirred solution of ethyl 1,1,1-trifluoro-2-(4-ethoxyphenyl)propionate (4.1 g) in toluene (100 cm$^3$) under a nitrogen atmosphere at −70° C. and the mixture stirred for a further 1 hour. After quenching with dilute hydrochloric acid the organic phase was separated, washed with water, dried over anhydrous magnesium sulphate, and concentrated by evaporation of the solvents under reduced pressure to give an oil which was purified by distillation at 0.2 mm using a kugelrohr apparatus (oven temperature 110°-130° C.) to yield 1,1,1-trifluoro-2-(4-ethoxyphenyl)-propan-3-ol as a colourless oil (2 g).

IR (liquid film): 3400 (broad), 1620, 1520, 1310, 1255, 1166, 1120, 1050 cm$^{-1}$

EXAMPLE 29

This Example illustrates the stages in the preparation of 1,1,1-trifluoro-2-(4-chlorophenyl)propan-3-ol.

Stage 1: Preparation of 1,1,1,3,3-pentafluoro-2-(4-chlorophenyl)-3-chloropropan-2-ol Chlorobenzene (31 g), chloropentafluoroacetone (50 g) and aluminium chloride (3 g) were placed in a digestion cell and heated in an autoclave at 120° C. for 8 hours. After cooling and venting, the crude mixture was poured into ice water and extracted into chloroform. The extracts were washed with water, dried over anhydrous magnesium sulphate and the solvents evaporated to leave a black oil (45 g). Analysis by gas liquid chromatography showed 2 main components, retention times 1.77 minutes (56%) and 10.71 minutes (32%). The volatile material was isolated by distillation in a kugelrohr apparatus at 0.1 mmHg, oven temperature 100°-120° C., to give a colourless oil 22.4 g.

$^1$H NMR (CDCl$_3$) δ (ppm): 7.0-7.4 (4H,ABq)

$^{19}$F NMR (CDCl$_3$) δ (ppm - relative to CFCl$_3$: −62.3 (2F,m); −73.8 (3F,t)

Stage 2: Preparation of 1,1,1,3,3-pentafluoro-2,3-dichloro-2-(4-chlorophenyl)propane Prepared as described in Stage 2 of Example 28 above, from 1,1,1,3,3-pentafluoro-2-(4-chlorophenyl)-3-chloropropan-2-ol.

GLC retention time: 1.95 minutes

Stages 3, 4, 5 and 6: Preparation of ethyl 1,1,1-trifluoro-2-(4-chlorophenyl)propionate and ethyl 1,1,1-trifluoro-2-(2,4-dichlorophenyl)propionate These stages were carried out as described in stages 3-6 of Examples 28 above. At the end of Stage 6, three principal reaction products were present in the reaction mixture:

Product A: Ethyl 1,1,1-trifluoro-2-(4-chlorophenyl)-propionate (GLC retention time: 2.59 minutes - 50%).

Product B: Ethyl 2-(4-chlorophenyl)acetate (GLC retention time: 3.05 minutes - 30%)

Product C: Ethyl 1,1,1-trifluoro-2-(2,4-dichlorophenyl)propionate (GLC retention time: 3.28 minutes - 10%)

Products A and C were isolated by preparative high pressure liquid chromatography, using n-hexane containing 4% by volume ethyl acetate as eluent.

Product A: $^1$H NMR (CDCl$_3$) δ (ppm): 1.18 (3H,t); 3.9-4.2 (3H,m); 7.04 (4H,s)

Product C: $^1$H NMR (CDCl$_3$) δ (ppm): 1.25 (3H,t); 4.1-4.3 (2H,m); 5.03 (1H,q); 7.2-7.6 (3H,m)

Stage 7: Preparation of 1,1,1-trifluoro-2-(4-chlorophenyl)propan-3-ol

Prepared as described in Stage 7 of Example 28 above from ethyl 1,1,1-trifluoro-2-(4-chlorophenyl)propionate GLC retention time: 2.12 minutes

EXAMPLE 30

This Example illustrates the preparation of 1,1,1-trifluoro-2-(2,4-dichlorophenyl)propan-3-ol.

This compound was prepared by the method described in stage 7 of Example 28 above, from ethyl 1,1,1-trifluoro-2-(2,4-dichlorophenyl)propionate. The starting material itself was product C, isolated in stage 6 of Example 29 above.

GLC retention time: 2.99 minutes.

EXAMPLE 31

This Example illustrates the preparation of 1,1,1-trifluoro-2-(4-ethoxyphenyl)propan-3-ol.

A solution of boron trifluoride etherate (0.12 cm$^3$) in tetrahydrofuran (2 cm$^3$) was added to a one molar (1M) solution of borane-methyl sulphide complex in tetrahydrofuran (1 cm$^3$) under an atmosphere of nitrogen. The temperature of the mixture was cooled to 0° C. by external cooling, and a solution of 1,1,1-trifluoro-2-(4-ethoxyphenyl)prop-2-ene oxide (0.1 g) in tetrahydrofuran 1 cm$^3$) was added with stirring. The mixture was allowed to warm to the ambient temperature (ca. 22° C.) and stirred overnight. The mixture was then partitioned between saturated potassium carbonate solution (6 cm$^3$) and diethyl ether (10 cm$^3$). The aqueous layer was separated and extracted twice with diethyl ether (10 cm$^3$). The combined organic layers were dried over anhydrous sodium sulphate and the solvent evaporated under reduced pressure to give a pale yellow oil (0.09 g). This oil was purified by column chromatography on a silica gel support, eluting with n-hexane containing 30% diethyl ether, to give 1,1,1-trifluoro-2-(4-ethoxyphenyl)propan-3-ol (0.05 g) as a colourless oil.

$^1$H NMR (CDCl$_3$) δ (ppm): 1.4 (3H,t); 1.6 (1H,broad s); 3.5 (1H,m); 4.0 (2H,q) overlapping with 2H,m); 7.0 (2H,d); 7.2 (2H,d)

IR (liquid film): 3400 (broad), 1620, 1520, 1310, 1255, 1166, 1120, 1050 cm$^{-1}$ GLC retention time: 6.06 minutes (50° C.-280° C. run)

EXAMPLE 32

This Example illustrates the preparation of 1,1,1-trifluoro-2-(4-ethoxyphenyl)-3-(3-phenoxybenzyloxy)propane from 1,1,1-trifluoro-2-(4-ethoxyphenyl)propan-3-ol.

A mixture of 1,1,1-trifluoro-2-(4-ethoxyphenyl)propan-3-ol (0.4 g), 3-phenoxybenzyl bromide (0.45 g), tetra-n-butylammonium hydrogen sulphate (0.05 g) and aqueous sodium hydroxide solution (40% w/v, 5.0 cm$^3$) was stirred at the ambient temperature for 6 hours after which it was partitioned between water and diethyl ether. The ethereal phase was separated, washed twice with water, dried over anhydrous magnesium sulphate and concentrated by evaporation of the solvent under reduced pressure. The residual oil (0.75 g) was purified by chromatography on a silica gel column eluted with a mixture of hexane (23 parts by volume) and ethyl acetate (2 parts by volume) to yield 1,1,1-trifluoro-2-(4-ethoxyphenyl)-3-(3-phenoxybenzyloxy) propane (0.21 g) as a viscous oil.

IR (liquid film): 1617, 1590, 1520, 1490, 1448, 1260, 1220, 1170, 1126, 1076, 1050, 700 cm$^{-1}$ $^1$H NMR (CDCl$_3$) δ (ppm): 1.42 (3H,t); 3.55 (1H,q); 3.8 (1H,m); 3.95 (1H,m); 4.0 (2H,q); 4.46 (ABq,2H); 6.8–7.4 (13H,m) $^{19}$F NMR (CDCl$_3$) δ (ppm - relative to CFCl$_3$): −68.43 (3F,d)

GLC retention time: 11.15 minutes.

EXAMPLE 33

By a procedure similar to that described in Example 32 above, the following compounds were prepared from the appropriate starting materials.

(i)  1,1,1-Trifluoro-2-(4-ethoxylphenyl)-3-(3-(4-bromophenoxy)benzyloxy)propane, from 1,1,1-trifluoro-2-(4-ethoxyphenyl)propan-3-ol and 3-(4-bromophenoxy)benzyl bromide.

The preparation of 3-(4-bromophenoxy)benzyl bromide is described in Example 34.

$^1$H NMR (CDCl$_3$) δ (ppm): 1.43 (3H,t); 3.4–4.1 (5H,m); 4.47 (2H,s); 4.8–7.5 (12H,m)

$^{19}$F NMR (CDCl$_3$) δ (ppm - relative to CFCl$_3$): −68.4 (CF$_3$,d)

GLC retention time: 12.53 minutes (ii)  1,1,1-Trifluoro-2-(4-ethoxyphenyl)-3-(3-(2,4-difluorophenoxy)benzyloxy)propane, from 1,1,1-trifluoro-2-(4-ethoxylphenyl)propan-3-ol and 3-(2,4-difluorophenoxy)benzyl bromide The preparation of 3-(2,4-difluorophenoxy)benzyl bromide is described in Example 35.

$^1$H NMR (CDCl$_3$) δ (ppm): 1.41 (3H,t); 3.56 (1H,m); 3.8 (1H,t); 3.98 (1H,dd); 4.03 (2H,q); 4.47 (2H,ABq); 6.8–7.3 (11H,m)

$^{19}$F NMR (CDCl$_3$) δ (ppm - relative to CFCl$_3$): −68.4 (CF$_3$,d); −115.4 (1F,m); −126.1 (1F,m)

GLC retention time: 10.65 minutes (iii)  1,1,1-Trifluoro-2-(4-ethoxyphenyl)-3-(3-(4-fluorophenylamino)benzyloxy)propane, from 1,1,1-trifluoro-2-(4-ethoxyphenyl)propan-3-ol and 3-(4-fluorophenylamino)benzyl bromide.

The preparation of 3-(4-fluorophenylamino)benzyl bromide is described in Example 36.

$^1$H NMR (CDCl$_3$) δ (ppm): 1.40 (3H,t); 3.56 (1H,m); 3.80 (1H,m); 3.99 (3H,m); 4.44 (2H,ABq); 5.52 (1H,broad s); 6.7–7.3 (12H,m)

$^{19}$F NMR (CDCl$_3$) δ (ppm - relative to CFCl$_3$): −68.4 (CF$_3$,d); −122.0 (1F,m)

GLC retention time: 11.92 minutes (iv)  1,1,1-Trifluoro-2-(4-chlorophenyl)-3-(3-phenoxybenzyloxy)propane, from 1,1,1-trifluoro-2-(4-chlorophenyl)propan-3-ol and 3-phenoxybenzyl bromide. In this case the compound was purified by high pressure liquid chromatography, eluting with n-hexane containing 20% by volume dichloromethane.

$^1$H NMR (CDCl$_3$) δ (ppm): 3.57 (1H,m); 3.8 (1H,t); 3.95 (1H,dd); 4.45 (2H,ABq); 6.8–7.4 (13H,m)

GLC retention time: 10.40 minutes (v)  1,1,1-Trifluoro-2-(2,4-dichlorophenyl)-3-(3-phenoxybenzyloxy)propane, from 1,1,1-trifluoro-2-(2,4-dichlorophenyl)propan-3-ol and 3-phenoxybenzyl bromide.

$^1$H NMR (CDCl$_3$) δ (ppm): 3.7–4.0 (2H,m); 4.3–4.5 (3H,m); 6.8–7.5 (12H,m)

$^{19}$F NMR (CDCl$_3$) δ (ppm - relative to CFCl$_3$)

GLC retention time: 10.97 minutes (vi)  1,1,1-Trifluoro-2-(4-ethoxyphenyl)-3-(3-benzylbenzyloxy)propane, from 1,1,1-trifluoro-2-(4-ethoxyphenyl)propan-3-ol and 3-benzylbenzyl bromide.

The preparation of 3-benzylbenzyl bromide is described in Example 37.

$^1$H NMR (CDCl$_3$) δ (ppm): 1.4 (3H,t); 3.55 (1H,m); 3.78 (1H,m); 3.9–4.1 (5H,m); 4.45 (2H,d); 6.85 (2H,d); 7.0–7.4 (11H,m)

$^{19}$F NMR (CDCl$_3$) δ (ppm - relative to CFCl$_3$): −68.45 (CF$_3$,d)

(vii)  1,1,1-Trifluoro-2-(4-ethoxyphenyl)-3-(3-phenoxy-4-fluorobenzyloxy)propane, from 1,1,1-trifluoro-2-(4-ethoxyphenyl)propan-3-ol and 3-phenoxy-4-fluorobenzyl bromide.

$^1$H NMR (CDCl$_3$) δ (ppm): 1.42 (t,3H); 3.55 (m,1H); 3.78 (m,1H); 3.95 (m,1H); 4.0 (q,2H); 4.43 (ABq, 2H); 6.8–7.4 (m,12H)

$^{19}$F NMR (CDCl$_3$) δ (ppm - relative to CFCl$_3$): −68.43 (d,3F,J$_{HF}$=8.38 Hz); −132.7 (m,1F).

IR (liquid film): 1616, 1595, 1518, 1486, 1253, 1216, 1170, 1135 cm$^{-1}$.

GLC retention time: 11.04 minutes.

EXAMPLE 34

This Example illustrates the stages in the preparation of 3-(4-bromophenoxy)benzyl bromide.

Stage 1: Preparation of 3-(4-bromophenoxy)benzaldehyde

This compound was prepared by a standard bromination reaction from 3-phenoxybenzaldehyde.

$^1$H NMR (CDCl$_3$) δ (ppm): 6.8–7.7 (8H,m); 10.0 (1H,s)

Stage 2: Preparation of 3-(4-bromophenoxy)benzyl alcohol.

This compound was prepared by a standard sodium borohydride reduction from 3-(4-bromophenoxy)benzaldehyde.

$^1$H NMR (CDCl$_3$) δ (ppm): 1.95 (1H,broad t - disappears on shaking with D$_2$O); 4.7 (2H, broad d, - collapses to singlet on shaking with D$_2$O); 6.8–7.6 (8H,m)

Stage 3: Preparation of 3-(4-bromophenoxy)benzyl bromide.

This compound was prepared from 3-(4-bromophenoxy)benzyl alcohol by a standard reaction with phosphorus tribromide.

$^1$H NMR (CDCl$_3$) δ (ppm): 4.43 (2H,s); 6.8–7.5 (8H,m)

EXAMPLE 35

The following Example illustrates the stages of the preparation of 3-(2,4-difluorophenoxy)benzyl bromide.

Stage 1: Preparation of 2-(3-(2,4-difluorophenoxy)phenyl)-1,3-dioxolane

A solution of 2,4-difluorophenol (10 g) in dry N,N-dimethylformamide (30 cm$^3$) was added dropwise, over 15 minutes to a suspension of sodium hydride (2.2 g, prepared from a 50% dispersion in oil (4.4 g) by washing with dry petroleum ether of boiling range 60°–80° C.) in dry N,N-dimethylformamide (20 cm$^3$); the addition was performed under an atmosphere of nitrogen at a temperature maintained at 0° C. After stirring for a further 10 minutes at 0° C., a solution of 2-(3-bromophenyl)-1,3-dioxolane (17.6 g, prepared by a standard reaction between 3-bromobenzaldehyde and ethylene glycol) in dry N,N-dimethylformamide (20 cm$^3$) was added at 0° C. over 5 minutes. A catalytic amount of anhydrous cuprous chloride was added, and the reaction mixture was heated at 100° C. for 28 hours. The mixture was cooled, added to water, and extracted with diethyl ether. The ether layers were washed firstly with sodium chloride solution, then 2 molar sodium hydroxide solution, and dried over anhydrous magnesium sulphate. Evaporation of the -TM solvent under reduced pressure gave 2-(3-(2,4-difluorophenoxy)phenyl)-1,3-dioxolane as an oil (8.5 g), which was used without further purification.

$^1$H NMR (CDCl$_3$) δ (ppm): ca. 3.95 (4H,m); 5.65 (1H,s); 6.6–7.5 (7H,m)

Stage 2: Preparation of 3-(2,4-difluorophenoxy)benzaldehyde.

Concentrated sulphuric acid (0.18 g) was added to a solution of 2-(3-(2,4-difluorophenoxy)phenyl)-1,3-dioxolane in acetone (200 cm$^3$). The stirred mixture was heated at 55° C. for 5 hours. After cooling, the solvent was evaporated under reduced pressure, and the residue neutralised by addition of an aqueous solution of sodium hydrogen carbonate. This aqueous mixture was partitioned between diethyl ether and water. The ether layer was separated, dried over anhydrous magnesium sulphate and the solvent evaporated under reduced pressure to give 3-(2,4-difluorophenoxy)benzaldehyde as an oil (6.4 g). The product was shown to be 85% pure by gas liquid chromatography, and was used without further purification.

$^1$H NMR (CDCl$_3$) δ (ppm): 6.8–8.0 (7H,m); 9.95 (1H,s)

Stage 3: Preparation of 3-(2,4-difluorophenoxy)benzyl alcohol.

Sodium hydroxide solution (2 molar, 0.5 cm$^3$) was added to a solution of 3-(2,4-difluorophenoxy)benzaldehyde (2 g) in methanol (20 cm$^3$) and the mixture was cooled to 0° C. Sodium borohydride (0.5 g) was added, and the mixture stirred for 30 minutes. After this time, water was added, and the mixture acidified to pH 4 by addition of dilute hydrochloric acid. This mixture was extracted with diethyl ether (5×50 cm$^3$). The combined organic layers were dried over anhydrous sodium sulphate, and the solvents evaporated under reduced pressure. The residue was purified by column chromatography on a silica gel support, using n-hexane containing 20% by volume ethyl acetate as eluent, to give 3-(2,4-difluorophenoxy)benzyl alcohol as a colourless oil.

$^1$H NMR (CDCl$_3$) δ (ppm): 1.7 (1H,t); 4.65 (2H,d); 6.8–7.4 (7H,m)

GLC retention time: 5.29 minutes

Stage 4: Preparation of 3-(2,4-difluorophenoxy)benzyl bromide 3-(2,4-Difluorophenoxy)benzyl alcohol (1.0 g) and triphenylphosphine (1.15 g) were dissolved in dry dichloromethane (40 cm$^3$ used in total) and the solution was cooled to −10° C. in an ice/salt bath. A solution of 1,2-dibromotetrachloroethane (1.5 g) in dichloromethane was added simultaneously with a solution of triethylamine in dichloromethane from separate dropping funnels, maintaining the temperature below 0° C. After 30 minutes the reaction was allowed to warm to room temperature. The mixture was poured into ice-cold water (70 cm$^3$), and after 5 minutes the layers were separated. The aqueous phase was extracted with dichloromethane (2×40 cm$^3$) and the combined organic layers were dried over anhydrous sodium sulphate and the solvent was removed by evaporation under reduced pressure. Analysis of the residue by gas liquid chromatography indicated a major component (75%) of triphenylphosphine oxide, the main Product (20%) with a GLC retention time of 5.65 minutes and a minor component (2–3%) with a GLC retention time of 4.99 minutes. Separation by chromatography on a silica gel support, eluting with n-hexane containing 10% by volume ethyl acetate, yielded a main product fraction (0.36 g) containing 71% 3-(2,4-difluorophenoxy)benzyl bromide and 29% of the minor component, which was identified by gas chromatography - mass spectrometry as 3-(2,4-difluorophenoxy)benzyl chloride. This mixture was used without further purification.

$^1$H NMR (CDCl$_3$) δ (p,)m): 4.43 (CH$_2$-Br,s); and 4.55 (CH$_2$-Cl,s) in a ratio of 26:10; 6.8–7.3 (7H,m)

EXAMPLE 36

This Example illustrates the stages in the preparation of 3-(4-fluorophenylamino)benzyl bromide.

Stage 1: Preparation of methyl 3-(4-fluorophenylamino)benzoate

4-Fluoroaniline (88 g), 3-iodobenzoic acid (40 g), potassium carbonate (24 g), cuprous chloride (2 g) and copper powder (4.5 g prepared as in Organic Syntheses Collective Volume II, p. 446), were mixed at room temperature, then heated up to 80° C. for 3 hours before allowing to cool overnight. The mixture was diluted in water (75 cm$^3$) containing potassium carbonate (5 g) and then steam distilled to remove the excess aniline (about 1 liter of distillate collected in 65 minutes). The residue was boiled with activated charcoal for 5 minutes, then cooled and filtered through celite. The celite was washed with dilute potassium carbonate solution. The filtrate was acidified with concentrated hydrochloric acid to pH 2, and the gummy solid that separated was dissolved in diethyl ether. The layers were separated and the aqueous layer was washed twice with diethyl ether. The combined organic layers were washed twice with water, dried over anhydrous sodium sulphate and the solvent evaporated under reduced pressure to give a dark blue oil (32 g). The oil was dissolved in methanol (133 cm$^3$) and concentrated sulphuric acid (7 cm$^3$) was added carefully. The mixture was heated at reflux for 90 minutes, then cooled and poured into water. The product was extracted into dichloromethane, and the organic layer separated and dried over anhydrous sodium sulphate. After evaporating the solvent under reduced pressure, the residual oil was purified by passing through a column of silica gel, eluting with dichloromethane. The product was crystallised from a dichloromethane - petroleum ether (boiling range 60°-80° C.) mixture to give methyl 3-(4-fluorophenylamino)benzoate (14 g) as large plates. A further 12 g of the substantially pure product was removed from the mother liquors.

$^1$H NMR (CDCl$_3$) δ (ppm): 3.9 (3H,s); 6.9-7.8 (9H,m).

Stage 2: Preparation of 3-(4-fluorophenylamino)benzyl alcohol.

The ester (4.85 g) was added to lithium borohydride (1g) in tetrahydrofuran (25 cm$^3$). The mixture was heated at the reflux temperature for 1 hour, when analysis by thin layer chromatography showed no trace of starting material. Water and dichloromethane were added and the mixture was poured into water. The layers were separated and the aqueous layer extracted with further portions of dichloromethane. The combined organic layers were washed with water, dried over anhydrous sodium sulphate, then the solvents were removed by evaporation under reduced pressure to give an oil that crystallised on scratching (4.7 g). Crystallisation from a mixture of dichloromethane and petroleum ether (boiling range 60°-80° C.) gave 3-(fluorophenylamino)benzyl alcohol (4.1 g).

$^1$H NMR (CDCl$_3$) δ (ppm): 4.60 (2H,s); 6.8-7.4 (10H,m)

Stage 3 : Preparation of 3-(4-fluorophenylamino)benzyl bromide 3-(4-Fluorophenylamino)benzyl alcohol (1.0 g) was dissolved in toluene (10 cm$^3$). A solution of phosphorous tribromide (0.42 g) in toluene (10 cm$^3$) was added dropwise. After a few moments, pyridine (0.36 g) in toluene was added dropwise. The reaction was stirred at room temperature for 2 hours, at which time no starting material could be detected by thin layer chromatography.

The mixture was poured into water and the products were extracted into chloroform. The combined organic extracts were washed with water then dried over anhydrous magnesium sulphate, then the solvents were evaporated under reduced pressure to leave a viscous oil (1.1 g). This oil was purified by passing through a short column of silica gel eluting with n-hexane contain 20% by volume ethyl acetate, to give 3-(4-fluorophenylamino)benzyl bromide (0.2 g). the product (rf. 0.8 on silica gel plates, with n-hexane containing 30% by volume ethyl acetate as eluent), was shown to contain minor impurities, but was used without further purification.

$^1$H NMR (CDCl$_3$) δ (ppm): major peaks at 4.43 (2H,s); 6.8-7.3 (8H,m)

EXAMPLE 37

This Example illustrates the stages in the preparation of 3-benzylbenzyl bromide.

Stage 1: Preparation of 2-(3-benzylbenzyl)-1,3-dioxolane.

This compound was prepared by a method analogous to that reported by Minato et al in Tetrahedron Letters, 21, 845, 1980.

Benzyl bromide (25.69 g) was added to a suspension of activated zinc powder (19.48 g) in dry tetrahdyrofuran (180 cm$^3$) under an atmosphere of nitrogen. The mixture was sonicated for 1 hour and then allowed to stand for a further hour. The solution was carefully decanted from the insoluble residue (under an atmosphere of nitrogen) into a second reaction vessel, and a mixture of 2-(3-bromophenyl)-1,3-dioxolane (10 g), palladium (Pd°) tetrakis triphenylphosphine (0.2 g) and tetrahydrofuran (50 cm$^3$) was added. The stirred mixture was heated at the reflux temperature for 5 hours, at which time analysis of the reaction mixture by gas liquid chromatography showed no trace of the principal starting materials. The mixture was cooled, added to diethyl ether, washed with ammonium chloride solution, water and brine, and dried over anhydrous magnesium sulphate. Evaporation of the solvents under reduced pressure gave the product as a yellow oil, which was purified by column chromatography on a silica gel support using petroleum ether (boiling range 60°-80° C.) containing 10% by volume (progressively increased to 20% by volume) of diethyl ether, to give 2-(3-benzylbenzyl)-1,3-dioxolane (8.2 g), which was immediately used in the next stage of the reaction.

Stage 2: Preparation of 3-benzylbenzaldehyde

A mixture of 2-(3-benzylbenzyl)-1,3-dioxolane (8.2 g), acetone (100 cm$^3$), water (10 cm$^3$) and concentrated sulphuric acid (20 drops) was stirred overnight, then added to diethyl ether. The resultant mixture was washed with sodium bicarbonate solution, water and brine, and dried over anhydrous magnesium sulphate. Evaporation of the solvents under reduced pressure gave 3-benzylbenzaldehyde (6.5 g), which was used without further purification.

$^1$H NMR (CDCl$_3$) δ (ppm): 4.0 (2H,s); 7.1-8.0 (9H,m): 10.0 (1H,s)

IR (liquid film): 1700 cm$^{-1}$ (C=O)

Stage 3: Preparation of 3-benzylbenzyl alcohol.

3-Benzylbenzaldehyde (5.5 g) was dissolved in methanol (75 cm$^3$) and cooled to 0° C. Sodium borohydride (1.29 g) was added gradually in small portions, and stirring was continued for one hour. The reaction mixture was cautiously poured into a water/diethyl ether mixture, and the resulting ethereal solution was washed with water and brine, and dried over anhydrous magnesium sulphate. Evaporation of the solvents under reduced pressure gave 3-benzylbenzyl alcohol as a pale yellow oil (5.2 g). The product was used without further purification.

$^1$H NMR (CDCl$_3$) δ (ppm): 1.8 (1H,broad s); 4.0 (2H,s); 4.6 (2H,s); 7.1-7.4 (9H,m)

IR (liquid film): 3350 cm$^{-1}$ (OH)

Stage 4 : Preparation of 3-benzylbenzyl bromide

A solution of 3-benzylbenzyl alcohol (1.98 g) in diethyl ether (60 cm$^3$) was cooled in an ice bath, and 1,1,2,2-tetrachloro-1,2-dibromoethane (3.90 g) added. When the addition was complete, triphenyl phosphine (3.14 g) was added to the cooled mixture. The reaction mixture was stirred for 10 minutes, then filtered and the solvent evaporated under reduced pressure. The resultant yellow oil was purified by column chromatography on a silica gel support, eluting with petroleum ether (boiling range 60°-80° C.) containing 10% by volume diethyl ether, to give 3-benzylbenzyl bromide (2.62 g).

60 MHz $^1$H NMR (CDCl$_3$) δ (ppm): 3.95 (2H,s): 4.45 (2H,s); 7.25 (9H,s)

EXAMPLE 38

This Example illustrates the stages in the preparation of 3-(4-bromophenoxy)-4-fluorobenzyl alcohol.

Stage 1: Preparation of 3-(4-bromophenoxy)-4-fluorobenzaldehyde

3-Phenoxy-4-fluorobenzaldehyde (2.16 g), bromine (1.6 g) and dry dichloromethane (20 cm$^3$) were mixed and stirred at the ambient temperature (ca. 22° C.) for 2 days. The mixture was then poured onto water and extracted with chloroform. The organic extracts were combined, washed once with saturated sodium metabisulphite solution and twice with water, then dried over anhydrous magnesium sulphate. The solvent was evaporated under reduced pressure to leave an oil (3.5 g). The product was purified by chromatography on a silica gel support, eluting with n-hexane containing 50% by volume ethyl acetate, to give 3-(4-bromophenoxy)-4-fluorobenzaldehyde (0.65 g) as an oil.

$^1$H NMR (CDCl$_3$) δ (ppm): ca. 6.9 (2H,m); 7.3–7.7 (5H,m); 9.9 (1H,s)

$^{19}$F NMR (CDCl$_3$) δ (ppm - relative to CFCl$_3$): −120.8 (1F,m)

GLC retention time: 6.87 minutes

Stage 2: Preparation of 3-(4-bromophenoxy)-4-fluorobenzyl alcohol.

This compound was prepared from 3-(4-bromophenoxy)-4-fluorobenzyl alcohol by a standard reduction using sodium borohydride.

$^1$H NMR (CDCl$_3$) δ (ppm): ca 1.7 (1H,broad s); 4.62 (2H,broad s); 6.8–7.5 (7H,m)

$^F$NMR (CDCl$_3$) δ (ppm - relative to CFCl$_3$): −132.7 (1F,m)

GLC retention time: 7.7 minutes

EXAMPLE 39

This Example illustrates the stages in the preparation of 3-(4-chlorophenoxy)-4-fluorobenzyl alcohol.

Stage 1: 3-Phenoxy-4-fluorobenzaldehyde (5 g) was dissolved in carbon tetrachloride (50 cm$^3$) containing chlorine (4.25 g) and the miture was stirred at room temperature for 48 hours. After pouring into water the mixture was extracted with chloroform. The combined extracts were washed with water then dried over anhydrous magnesium sulphate and the solvent evaporated under reduced pressure to leave an oil (5.5 g). This material was purified by high pressure liquid chromatograhy on a silica gel support eluting with n-hexane containing 10% by volume ethyl acetate, to give 3-(4-chlorophenoxy)-4-fluorobenzylaldehyde as an oil (1.8 g).

$^1$H NMR (CDCl$_3$) δ (ppm): 6.95 (1H,m); ca. 7.35 (4H,m); 7.54 (1H,dd); 7.7 (1H,ddd); 9.9 (1H,s)

GLC retention time: 6.25 minutes

Stage 2: Preparation of 3-(4-chlorophenoxy)-4-fluorobenzyl alcohol 3-(4-Chlorophenoxy)-4-fluorobenzaldehyde (1.8 g) was dissolved in methanol (10 cm$^3$) and cooled to 10° C. Sodium borohydride (0.3 g) in a mixture of water (3 cm$^3$) and 2 molar sodium hydroxide solution (0.4 cm$^3$) was added dropwise, and the mixture stirred at room temperature for 1¼ hours. The mixture was then acidified with dilute sulphuric acid and extracted with chloroform. The combined organic extracts were washed with water, dried over anhydrous magnesium sulphate and the solvent evaporated under reduced pressure to leave a viscous oil (1.8 g). This oil was purified by chromatography on a silica gel support, eluted with n-hexane containing 25% by volume ethyl acetate to give 3-(4-chlorophenoxy)-4-fluorobenzyl alcohol as a white solid (1.45 g).

$^1$H NMR (CDCl$_3$) δ (ppm): 1.7 (1H,broad t); 4.6 (2H,broad d); 6.8–7.4 (7H,m)

$^{19}$F NMR (CDCl$_3$) δ (ppm - relative to CFCl$_3$): −132.7 (1F,m)

GLC retention time: 7.10 minutes

EXAMPLE 40

This Example illustrates the stages in the preparation of 3-benzyl-4-fluorobenzyl alcohol.

Stage 1: Preparation of 3-bromo-4-fluorobenzaldehyde

A solution of 4-fluorobenzaldehyde (49.6 g) in dry dichloromethane (20 cm$^3$) was added to a cooled (0° C.) suspension of powdered aluminium trichloride (90.4 g) in dry dichloromethane (100 cm$^3$). Bromine (70.4 g) was added, and the mixture heated at the reflux temperature for 16 hours. After cooling, the reaction mixture was carefully poured onto ice and extracted with dichloromethane. The combined organic layers were washed with saturated sodium metabisulphite solution, water and brine, then dried over anhydrous magnesium sulphate. Evaporation of the solvent under reduced pressure gave a dark red oil, which was purified by distillation under reduced pressure, using a 4" Vigreux column to give 3-bromo-4-fluorobenzaldehyde (45.7 g) as an oil, boiling point 85°–108° C. at 8 mmHg.

Stage 2: Preparation of 2-(3-bromo-4-fluorophenyl)-1,3-dioxolane

A mixture of 3-bromo-4-fluorobenzaldehyde (45.7 g), ethylene glycol (27.93 g), p-toluenesulphonic acid (0.225 g) and dry toluene (110 cm$^3$) was heated at the reflux temperature under a Dean and Stark trap. After 4.5 hours, approximately 12 cm$^3$ of water had collected in the trap, and analysis of the reaction mixture by gas liquid chromatography indicated that no starting aldehyde was present. The mixture was cooled and poured into diethyl ether, washed with saturated sodium bicarbonate solution and brine, and dried over anhydrous magnesium sulphate. Evaporation of the solvent under reduced pressure gave a yellow oil, which was purified by distillation under reduced pressure to give 2-(3-bromo-4-fluorophenyl)-1,3-dioxolane (43.56 g), boiling point 68°–106° C. at 0.004 mmHg.

90 MHz $^1$H NMR (CDCl$_3$) δ (ppm ): 4.1 (4H,m); 5.8 (1H,s); 7.0–7.7 (3H,m)

Stage 3: Preparation of 2-(3-benzyl-4-fluorophenyl)-1,3-dioxolane

This compound was prepared by a method analogous to that reported by Minato et al in Tetrahedron Letters, 21, 845, 1980.

Benzyl bromide (2.77 g) was added in one addition to a suspension of activated zinc powder (2.1 g) in dry tetrahydrofuran (20 cm$^3$) under an atmosphere of nitrogen. The reaction mixture was sonicated for 2 hours, allowed to stand for 30 minutes and carefully filtered under an atmosphere of nitrogen. The filtered solution was then added to a mixture of 2-(3-bromo-4-fluorophenyl)-1,3-dioxolane (1 g) and palladium (Pd°) tetrakis triphenyl phosphine (0.05 g) in dry tetrahydrofuran (10 cm$^3$) under an atmosphere of nitrogen. The stirred mixture was heated at the reflux temperature for 48 hours, at which time analysis by gas liquid chromatography showed no trace of starting material. The reaction mixture was cooled and poured into diethyl ether. The organic layer was separated, and washed with ammonium chloride solution, water and brine, then dried over anhydrous magnesium sulphate. Evaporation of the solvent under reduced pressure gave a yellow oil which was purified by column chromatography on a silica gel support, using petroleum ether (boiling range 40°–60°

C.) containing diethyl ether (progressively increased from 10% to 20% by volume) as eluent, to give 2-(3-benzyl-4-fluorophenyl)-1,3-dioxolane (0.7 g). The product was used without further purification.

60 HMz $^1$H NMR (CDCl$_3$) δ (ppm): 4.0 (6H,m); 5.7 (1H,s); 6.8–7.5 (8H,m)

Stage 4: Preparation of 3-benzyl-4-fluorobenzaldehyde

A mixture of 2-(3-benzyl-4-fluorophenyl)-1,3-dioxolane (0.7 g) acetone (10 cm$^3$), water (1 cm$^3$) and concentrated sulphuric acid (5 drops) was stirred overnight. The reaction mixture was poured into diethyl ether and the organic layer washed with sodium bicarbonate solution, water and brine, then dried over anhydrous magnesium sulphate. Evaporation of the solvents under reduced pressure gave 3-benzyl-4-fluorobenzaldehyde (0.59 g), which was used without further purification.

$^1$H NMR (CDCl$_3$) δ (ppm): 4.10 (2H,s); 7.20 (6H,m); 7.75 (2H,m); 9.90 (1H,s)

IR (liquid film): 1700 cm$^{-1}$ (C=O)

Stage 5: Preparation of 3-benzyl-4-fluorobenzyl alcohol

A solution of 3-benzyl-4-fluorobenzaldehyde (5 g) in methanol (75 cm$^3$) was cooled to 0° C. Sodium borohydride (1.34 g) was added in portions, and the mixture stirred for 1 hour. The reaction mixture was then poured cautiously into a mixture of water and diethyl ether, and the organic layer was separated, washed with water and brine, and dried over anhydrous magnesium sulphate. Evaporation of the solvents under reduced pressure gave a pale yellow oil which was purified by distillation in a kugelrohr apparatus to give 3-benzyl-4-fluorobenzyl alcohol (4.0 g).

Boiling point: 120° C. at 0.02 mmHg $^1$H NMR (CDCl$_3$) δ (ppm): 1.7 (1H,broad s); 4.0 (2H,s); 4.6 (2H,s); 7.0–7.3 (8H,m)

IR (liquid film): 3600–3100 cm$^{-1}$ (OH)

EXAMPLE 41

This Example illustrates the preparation of 4-bromobenzyl methyl ether.

4-Bromobenzyl alcohol (1.87 g) was added over 10 minutes to a stirred suspension of sodium hydride (0.24 g - used directly in the form of 0.48 g of a 50% dispersion in oil) in dry N,N-dimethylformamide (10 cm$^3$) under an atmosphere of nitrogen. After evolution of hydrogen had ceased (20 minutes), methyl iodide (1.42 g) was added and the reaction mixture was stirred for a further 10 minutes. The mixture was poured into water and the organic layer separated. The aqueous layer was extracted with diethyl ether. The combined organic layers were dried over anhydrous sodium sulphate, and concentrated by evaporation under reduced pressure. The residual, crude product was purified by column chromatography on a silica gel support, eluting with n-hexane containing 12.5% by volume ethyl acetate, to give 4-bromobenzyl methyl ether (1.6 g).

$^1$H NMR (CDCl$_3$) δ (ppm): 3.44 (3H,s); 4.46 (2H,s); ca. 7.3 (4H,ABq)

GLC retention time: 2.00 minutes.

EXAMPLE 42

This Example illustrates the stages in the preparation of 4-bromo-2-fluorophenetole.

Stage 1: Preparation of 4-bromo-2-fluorophenol.

A solution of bromine (140.6 g) in carbon disulphide (50 cm$^3$) was added over 3 hours to a stirred solution of 2-fluorophenol (89.68 g) in carbon disulphide (150 cm$^3$), the temperature being maintained at ca. 10° C. throughout the addition by external cooling. The reaction mixture was allowed to stand at the ambient temperature (ca. 20° C.) for 18 hours, and was then poured into an aqueous solution of sodium metabisulphite (100 cm$^3$). The organic layer was separated, washed with aqueous sodium bicarbonate solution (2×100 cm$^3$) and dried over anhydrous sodium sulphate. Removal of the solvent by evaporation under reduced presure gave an oil, which was purified by distillation under reduced pressure to give two fractions, each shown by gas liquid chromatography to contain 97% 4-bromo-2-fluorophenol. Fraction 1 (89.3 g) : boiling range 85°–86° C. (ca. 15 mmHg) Fraction 2 (47.5 g): boiling range 86°–87° C. (ca. 15 mmHg)

The fractions were further shown by gas liquid chromatography to contain, respectively, 1% and 1.5% of dibrominated material.

$^1$H NMR (CDCl$_3$) δ (ppm): 5.3 (1H,broad s); 6.9 (1H,t); 7.1–7.3 (2H,m)

Stage 2: Preparation of 4-bromo-2-fluorophenetole.

A mixture of 2-fluoro-4-bromophenol (19.1 g), sodium hydroxide (6 g), ethyl iodide (46.8 g), tetra-n-butylammonium bromide (3.2 g), dichloromethane (250 cm$^3$) and water (250 cm$^3$) was stirred vigorously at the ambient temperature for 5½ hours, then allowed to stand for a further 68 hours. The organic layer was separated and the aqueous layer was washed with dichloromethane; the combined organic layers were then dried over anhydrous sodium sulphate. The solvent was removed by evaporation under reduced Pressure at a bath temperature maintained below 40° C. The residual oil was purified by column chromatography on a silica gel support, eluting firstly with n-hexane and secondly with dichloromethane. The product-containing fractions were combined, washed with an aqueous solution of sodium metabisulphite, dried over anhydrous sodium sulphate and concentrated by evaporation under reduced pressure to give 4-bromo-2-fluorophenetole (15.2 g) as an oil. The product was shown by gas liquid chromatography to be 93% pure, and was used without further purification.

$^1$H NMR (CDCl$_3$) δ (ppm): 1.45 (3H,t); 4.07 (2H,q); 6.7–7.3 (3H,m)

$^{19}$F NMR (CDCl$_3$) δ (ppm - relative to CFCl$_3$): −131.8 (1F,m)

EXAMPLE 43

This Example illustrates the resolution of (±)-1,1,1-trifluoro-2-(4-ethoxyphenyl)-3-(3-phenoxybenzyloxy) propane.

(±)-1,1,1-trifluoro-2-(4-ethoxyphenyl)-3-(3-phenoxybenzyloxy)propane was resolved by high pressure liquid chromatography, using a Pirkle type 1A column (25 cm×4.9 mm) at −20° C., and n-hexane containing 1% by volume chloroform as eluent, at a flow rate of 0.7 cm$^3$/minute. Elution was monitored using a UV detector at 220 mm. Two isomers were detected: isomer A (retention time ca. 51 minutes) and isomer B (retention time ca. 54.6 minutes). A total of three fractions were collected.

Fraction 1 (10 mg): 92.9% isomer A, 7.1% isomer B
Fraction 2 (17 mg): 19.7% isomer A, 80.3% isomer B
Fraction 3 (9 mg): 12.5% isomer A, 87.1% isomer B Optical rotations were measured for fraction 1 (at a concentration of 10 mg in 1.5 ml) and for fraction 3 (at a concentration of 9 mg in 1.5 ml).

The observed angles of rotation were small, (ca. 0.01°) and similar in magnitude to the limits of determination of the apparatus used. On the basis of repeated observations, isomer A was assigned the dexrorotatory designation: (+)-1,1,1-trifluoro-2-(4-ethoxyphenyl)-3-(3-phenoxybenzyloxy)propane, and isomer B the laevorotatory designation: (−)-1,1,1-trifluoro-2-(4-ethoxyphenyl)-3-(3-phenoxybenzyloxy) propane.

Insecticidal evaluation of fraction 1 and fraction 3 indicates that isomer A is substantially more active than isomer B. It is thus believed that in this series of compounds insecticidal activity is principally associated with the isomer having an absolute configuration corresponding to that of isomer A herein.

EXAMPLE 44

This Example illustrates the insecticidal properties of the Products of this invention.

The activity of the product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment. In the case of the species *Musca domestica* (housefly), additional tests to determine the knockdown effect of the compounds were performed. Details are given in Table III.

The results of the tests are given in Table IV for each of the Products, at the rate in parts per million given in the second column as a grading of mortality designated as A, B or C wherein A indicates 80–100% mortality or knockdown (70–100% in the case of *Spodoptera exigua*), B indicates 50–79% mortality or knockdown (50–69% in the case of *Spodoptera exigua*) and C indicates less than 50% mortality or knockdown.

In Table IV the pest organism used is designated by a letter code and the pest species, the support medium or food, and the type and duration of test is given in Table III.

TABLE III

| CODE LETTERS (Table IV) | TEST SPECIES | SUPPORT MEDIUM/FOOD | TYPE OF TEST | DURATION (days) |
| --- | --- | --- | --- | --- |
| TU | *Tetranychus urticae* (red spider mites - adult) | French bean leaf | Contact | 3 |
| MP | *Myzus persicae* (aphids) | Leaf | Contact | 2 |
| NL | *Nilaparvata lugens* (green leaf hopper) | Cabbage leaf | Contact | 6 |
| HV | *Heliothis viriscens* (tobacco budworm) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| MD/KD | *Musca domestica* (houseflies - adults) | Cotton wool/ sugar | Knockdown | 4 hours |
| SE | *Spodoptera exigua* (lesser armyworm) | Cotton leaf | Residual | 3 |

"Contact" test indicates that both pests and medium were treated and "residual" indicates that the medium was treated before infestation with the pests.

TABLE IV

| COMPOUND NO. | RATE (ppm) | TU | MP | NL | MD KD | MD | BG | HV | SE | DB |
| --- | --- | --- | --- | --- | --- | --- | --- | --- | --- | --- |
| 1 | 500 | A | A | A | A | A | A | A | — | A |
| 2 | 500 | C | B | A | C | B | A | C | — | A |
| 3 | 250 | C | A | A | A | A | A | C | — | A |
| 4 | 100 | — | A | A | A | A | A | A | — | A |
| 5 | 500 | B | A | A | A | A | A | A | — | A |
| 6 | 500 | A | A | A | A | A | A | A | — | A |
| 7 | 500 | A | A | A | A | A | A | C | — | A |
| 8 | 500 | C | A | A | A | A | A | A | A | A |
| 9 | 250 | B | C | C | A | A | A | A | — | A |
| 10 | 250 | C | B | A | A | A | A | A | A | A |
| 11 | 500 | C | C | A | A | B | B | C | B | C |
| 12 | 500 | C | A | A | A | A | A | A | A | A |
| 13 | 100 | C | A | A | A | A | A | A | A | B |
| 14 | 100 | C | A | A | A | A | A | A | A | A |
| 15 | 500 | A | A | A | A | A | A | — | — | A |
| 16 | 100 | C | A | A | A | A | A | A | — | A |
| 18 | 250 | A | A | A | A | A | A | A | A | A |
| 19 | 250 | C | A | A | A | A | A | A | — | A |
| 20 | 100 | A | A | A | A | A | A | A | — | A |
| 21 | 500 | A | A | C | A | A | B | A | A | A |
| 22 | 500 | C | — | A | A | A | A | B | A | A |
| 23 | 500 | C | B | A | A | B | C | C | A | A |

TABLE IV-continued

| COMPOUND NO. | RATE (ppm) | TU | MP | NL | MD KD | MD | BG | HV | SE | DB |
|---|---|---|---|---|---|---|---|---|---|---|
| 24 | 100 | C | A | A | A | A | A | B | A | A |
| 25 | 100 | A | A | A | A | A | A | A | A | A |
| 26 | 100 | A | B | A | A | A | A | A | — | A |
| 27 | 100 | A | A | A | C | A | A | A | — | A |
| 28 | 100 | C | A | A | A | A | A | A | A | A |
| 29 | 100 | C | A | A | A | A | A | A | — | A |
| 30 | 500 | C | C | A | A | A | A | A | — | A |
| 31 | 500 | C | A | A | A | A | A | A | A | A |
| 32 | 500 | C | B | A | A | A | B | A | A | A |
| 33 | 500 | A | A | A | A | A | A | A | — | A |
| 38 | 100 | C | A | B | C | A | A | A | — | C |
| 39 | 250 | — | C | A | C | C | C | C | — | C |
| 40 | 250 | — | A | A | A | A | A | A | — | A |
| 41 | 500 | — | A | A | A | A | C | A | — | A |
| 42 | 250 | C | A | A | A | A | A | A | — | B |
| 43 | 500 | B | A | A | A | A | B | — | — | C |
| 44 | 500 | C | A | A | A | A | A | A | — | B |
| 45 | 250 | B | C | C | A | C | C | C | — | C |
| 46 | 500 | C | C | C | A | C | C | C | — | C |
| 50 | 500 | C | A | A | A | A | C | A | — | A |
| 51 | 100 | C | C | B | C | C | C | A | A | A |
| 52 | 500 | C | C | C | A | B | A | B | — | C |
| 53 | 500 | A | A | A | A | A | A | — | — | A |
| 59 | 100 | A | C | A | A | A | A | A | — | A |
| 60 | 100 | C | B | A | C | C | A | A | A | C |
| 61 | 100 | A | A | A | A | A | A | A | A | A |
| 64 | 500 | C | C | C | B | B | C | A | C | C |
| 65 | 500 | C | C | C | C | C | A | A | B | C |
| 75 | 100 | — | B | A | A | B | C | C | — | A |
| 76 | 500 | — | A | A | A | A | A | A | — | A |
| 77 | 250 | — | A | A | A | A | A | A | — | A |
| 78 | 250 | — | C | A | C | C | A | A | — | A |
| 79 | 250 | C | C | A | A | A | A | A | — | C |
| 80 | 500 | C | A | A | A | A | A | C | — | A |
| 81 | 500 | C | A | A | A | A | — | — | — | A |
| 82 | 500 | C | A | C | A | A | A | A | — | A |
| 83 | 500 | C | A | A | A | A | A | A | A | A |
| 84 | 500 | A | A | A | A | A | A | A | A | A |
| 112 | 250 | C | C | C | B | C | C | C | — | A |
| 113 | 250 | — | C | B | A | B | C | C | — | A |
| 114 | 100 | — | C | B | C | C | C | C | — | C |
| 116 | 500 | A | C | C | B | B | C | — | — | C |
| 117 | 500 | C | C | C | A | B | C | C | — | C |
| 120 | 500 | C | C | C | A | C | C | C | C | C |
| 124 | 500 | A | C | C | C | C | C | C | — | C |
| 126 | 500 | A | C | C | A | C | C | — | — | C |
| 127 | 500 | C | C | C | A | B | C | C | B | A |
| 128 | 500 | C | C | C | C | B | C | A | A | B |
| 129 | 500 | C | B | A | A | A | C | B | A | C |
| 135 | 250 | C | C | C | A | C | C | A | A | C |
| 136 | 500 | C | C | C | A | A | C | B | C | A |
| 137 | 500 | C | A | C | C | C | C | C | A | C |
| 139 | 500 | — | C | C | A | A | C | A | — | A |
| 141 | 500 | — | C | B | A | A | C | A | — | B |
| 142 | 500 | A | C | C | C | C | C | A | — | C |
| 149 | 250 | — | C | B | C | C | C | B | — | C |
| 150 | 250 | — | B | C | C | C | C | A | — | A |
| 163 | 500 | C | C | A | A | A | B | A | — | A |
| 164 | 500 | A | C | C | B | C | C | C | — | A |
| 165 | 500 | C | C | B | C | C | A | C | — | B |
| 167 | 100 | C | C | C | A | A | A | A | A | B |
| 168 | 500 | C | A | C | C | C | A | A | — | A |

We claim:
1. A compound of formula:

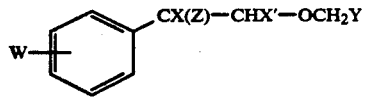

(I)

wherein W represents one or two substituents selected from halo, alkyl, alkoxy, alkoxyalkyl, haloalkyl and haloalkoxy, or W represents a bidentate group linking adjacent carbon atoms selected from alkylene of 3 or 4 carbon atoms and alkylenedioxy of up to 2 carbon atoms; Z represents trifluoromethyl; Y represents a substituted aryl group where each substituent is selected from halo, alkyl, aryl, aralkyl, aryloxy and arylamino; and either X' is hydrogen and X is selected from hydrogen, halo, hydroxy, alkoxy and aryloxy, or X and X' together represent a second bond between the adjacent carbon atoms.

2. A compound according to claim 1 wherein W is fluoro, chloro, bromo, alkyl of up to four carbon atoms, alkoxy of up to four carbon atoms, alkoxyalkyl of up to a total of four carbon atoms, fluoroalkyl of up to two carbon atoms, fluoroalkoxy of up to two carbon atoms, alkylene of three or four carbon atoms, or alkylenedioxy of up to two carbon atoms, and Y represents an aryl group selected from phenyl, pyridyl and furyl, substituted with fluoro, methyl, phenyl, benzyl, phenoxy, chlorophenoxy, fluorophenoxy, bromophenoxy, or fluoroanilino.

3. A compound according to claim 1 wherein W is 4-fluoro, 4-chloro, 4-bromo, 2,4-dichloro, 4-methyl, 4-n-propyl, 4-t-butyl, 4-methoxy, 4-ethoxy, 4-methoxymethyl, 4-trifluoromethyl, 4-trifluoromethoxy, 4-difluoromethoxy, 3-fluoro-4-ethoxy, 3,4-trimethylene or 3,4-methylenedioxy, X is hydrogen, chloro, fluoro, hydroxy, methoxy or acetoxy, and X' is hydrogen; Y is 3-phenoxyphenyl, 3-(4-chlorophenoxy)phenyl, 4-fluoro-3-phenoxyphenyl, 3-(4-bromophenoxy)phenyl, 4-fluoro-3-(4-bromophenoxy)phenyl, 4-fluoro-3-(4-chlorophenoxy)phenyl, 3-(2,4-difluorophenoxy)phenyl, 3-benzylphenyl, 4-fluoro-3-benzylphenyl, 3-(4-fluorophenylamino)phenyl, 6-phenoxypyrid-2-yl, 2-methyl-3-phenylphenyl, 4-methyl-2,3,5,6-tetrafluorophenyl, or 5-benzylfuran-3-yl.

4. A compound according to claim 1 wherein W is 4-chloro, 4-n-propyl, 4-t-butyl, 4-trifluoromethoxy, 4-difluoromethoxy, or 3,4-trimethylene, Y is 3-phenoxyphenyl, 3-(4-chlorophenoxy)phenyl or 4-fluoro-3-phenoxyphenyl, and X and X' represent a second bond between the adjacent carbon atoms.

5. A compound according to claim 1 selected from the group of compounds consisting of 1,1,1-trifluoro-2-(4-ethoxyphenyl)-3-(4-fluoro-3-phenoxybenzyloxy)propane, 1,1,1-trifluoro-2-(4-ethoxyphenyl)-3-[3-(4-chlorophenoxy)benzyloxy]propane, 1,1,1-trifluoro-2-(4-trifluoromethylphenyl)-3-(4-fluoro-3-phenoxybenzyloxy)propane, 1,1,1-trifluoro-2-(4-trifluoromethylphenyl)-3-[3-(4-chlorophenoxy)benzyloxy]propane, 1,1,1-trifluoro-2-(4-trifluoromethoxyphenyl)-3-(4-chlorophenoxy)phenoxybenzyloxy)propane and 1,1,1-trifluoro-2-(4-trifluoromethoxyphenyl)-3-[3-(4-chlorophenoxy)benzyloxy]propane.

6. An insecticidal composition comprising an insecticidally effective amount of a compound as defined in claim 1 in association with an insecticidally inert diluent or carrier.

7. A method of combating insect pests at a locus which comprises applying to the locus an insecticidally effective amount of a composition as defined in claim 6.

8. A process for preparing a compound of formula:

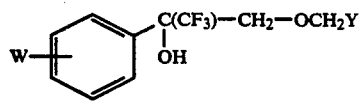

wherein W and Y are as defined in claim 1, comprises either (i) reacting a compound of formula:

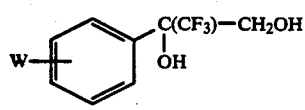

with a compound of formula:

Y—CH₂—Hal or (ii) reacting a compound of formula:

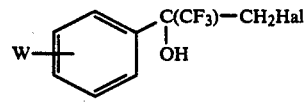

with a compound of formula:

Y—CH₂OH or (iii) reacting a compound of formula:

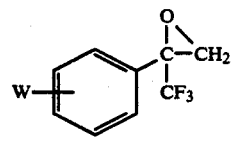

with a compound of formula:

Y—CH₂OH and thereafter, if desired converting the product (a) to a compound of formula:

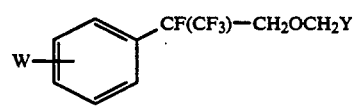

by reacting with a fluorinating agent; or
(b) to a compound of formula:

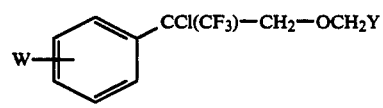

and/or a compound of formula:

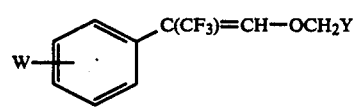

by reaction with an inorganic acid chloride, or
(c) to an O-alkyl derivative by reaction with an alkyl halide and a base, or
(d) to an O-acyl derivative by reaction with an acyl chloride or acyl anhydride, wherein Hal represents chloro or bromine.

9. A process for preparing a compound of formula:

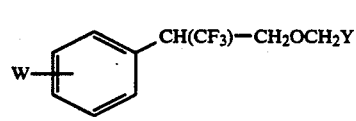

which comprises treating the corresponding compund of formula:

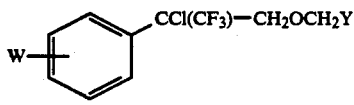

with a trialkyltin hydride.

10. A process for preparing a compound of formula:

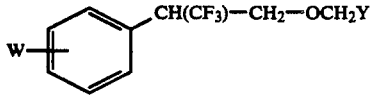

which comprises reacting a compound of formula:

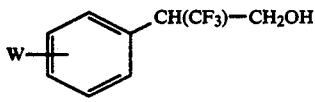

with a compound of formula:

YCH$_2$Hal where Hal represents chloro or bromo.

11. An alkoxyalkane derivative of the formula:

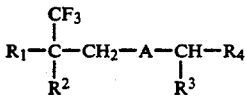

wherein in

R$_1$ is phenyl substituted by C$_{1-4}$ alkyl, fluoro-C$_{1-2}$ alkyl, C$_{3-4}$ alkenyl, C$_{1-4}$ alkoxy, fluoro-C$_{1-2}$ alkoxy and halo;

R$_2$ is hydrogen;
A is oxygen;
R$_3$ is hydrogen; and
R$_4$ is phenyl or pyridyl or these groups substituted by methyl, benzyl, phenoxy, halophenoxy, fluoroanilino, phenyl and fluoro 12. Alkoxylane derivative according to claim 11 in which
R$_1$ is chlorophenyl, bromophenyl, fluorophenyl, methylphenyl, methoxyphenyl, ethoxyphenyl or difluoromethoxyphenyl,
R$_2$ is hydrogen;
R$_3$ is hydrogen;
R$_4$ is phenoxyphenyl, fluorophenoxyphenyl or phenoxypyridyl; and
A is oxygen.

13. Insecticidal and acaricidal composition which comprises a compound claimed in claim 11 in admixture with an agriculturally acceptable diluent.

14. A method of combating insects and acarids which comprises applying to the insects or acarids or their locus an effective amount of a compound claimed in claim 11.

15. The method of claim 14 in which said compound is [2-(4-ethoxyphenyl)-2-trifluoroethyl] (4-fluoro-3-phenoxybenzyl)ether.

16. A method of combating insects and acarids which comprises applying to the insects or acarids or to their locus an effective amount of a compound claimed in claim 12.

17. Insecticidal and acaricidal composition according to claim 13 in which said compound is [2-(4-ethoxyphenyl)-2-trifluoroethyl] (4-fluoro-3-phenoxybenzyl)ether.

18. Insecticidal and acaricidal composition which comprises a compound claimed in claim 12 in admixture with an agriculturally acceptable diuent.

19. Alkoxyalkane derivative according to claim 11 which is [2-(4-ethoxyphenol)-2-trifluoroethyl] (4-fluoro-3-phenoxybenzyl)ether.

* * * * *